US009389229B2

(12) United States Patent
Patel et al.

(10) Patent No.: US 9,389,229 B2
(45) Date of Patent: Jul. 12, 2016

(54) METHODS FOR DETECTING AND MEASURING AGGREGATION

(71) Applicant: THERANOS, INC., Palo Alto, CA (US)

(72) Inventors: Paul Patel, Palo Alto, CA (US);
Samartha Anekal, Palo Alto, CA (US);
Ian Gibbons, Palo Alto, CA (US);
Elizabeth A. Holmes, Palo Alto, CA (US)

(73) Assignee: Theranos, Inc., Palo Alto, CA (US)

( * ) Notice: Subject to any disclaimer, the term of this patent is extended or adjusted under 35 U.S.C. 154(b) by 17 days.

(21) Appl. No.: 13/944,857

(22) Filed: Jul. 17, 2013

(65) Prior Publication Data

US 2014/0045170 A1 Feb. 13, 2014

Related U.S. Application Data

(60) Provisional application No. 61/673,215, filed on Jul. 18, 2012.

(51) Int. Cl.
*G01N 33/556* (2006.01)
*G01N 33/543* (2006.01)
*G01N 33/569* (2006.01)
*G01N 33/68* (2006.01)
*B01L 3/00* (2006.01)

(52) U.S. Cl.
CPC ........ *G01N 33/556* (2013.01); *G01N 33/54313* (2013.01); *G01N 33/56983* (2013.01); *G01N 33/6854* (2013.01); *B01L 3/5021* (2013.01)

(58) Field of Classification Search
None
See application file for complete search history.

(56) References Cited

U.S. PATENT DOCUMENTS

| | | | |
|---|---|---|---|
| 4,176,174 A | 11/1979 | Russell et al. | |
| 4,197,088 A | 4/1980 | Meserol et al. | |
| 4,298,346 A | 11/1981 | Ito | |
| 4,403,037 A * | 9/1983 | Coates | 435/5 |
| 4,556,641 A | 12/1985 | Kano et al. | |
| 4,829,011 A | 5/1989 | Gibbons | |
| 5,169,601 A | 12/1992 | Ohta et al. | |
| 5,227,312 A | 7/1993 | Grundy | |
| 5,330,897 A | 7/1994 | Pindak et al. | |
| 5,541,417 A * | 7/1996 | Xiong et al. | 250/559.05 |
| 5,994,139 A | 11/1999 | Jacobs et al. | |
| 6,992,819 B2 | 1/2006 | Vodyanoy | |
| 7,026,131 B2 | 4/2006 | Hurt et al. | |
| 7,087,203 B2 | 8/2006 | Gordon et al. | |
| 7,718,420 B2 | 5/2010 | Kim et al. | |
| 8,007,999 B2 | 8/2011 | Holmes et al. | |
| 8,435,738 B2 | 5/2013 | Holmes et al. | |
| 2001/0034068 A1 | 10/2001 | Spivey et al. | |
| 2008/0212865 A1 | 9/2008 | Zhu et al. | |
| 2009/0053688 A1 | 2/2009 | Bystryak et al. | |
| 2009/0053740 A1 | 2/2009 | Stoika et al. | |
| 2009/0155823 A1 | 6/2009 | Bunce et al. | |
| 2009/0214114 A1 | 8/2009 | Bengtsson et al. | |
| 2009/0317793 A1 | 12/2009 | Jonsmann et al. | |
| 2009/0325148 A1 | 12/2009 | Kachurin et al. | |
| 2010/0137159 A1 | 6/2010 | Kapil et al. | |
| 2010/0183216 A1 | 7/2010 | Yamada | |
| 2010/0221757 A1 | 9/2010 | Jacobs et al. | |
| 2011/0013821 A1 | 1/2011 | Mimura et al. | |
| 2011/0045492 A1 | 2/2011 | Bau-Madsen et al. | |
| 2011/0097705 A1 | 4/2011 | Kachurin et al. | |
| 2011/0229914 A1 | 9/2011 | Lee et al. | |
| 2015/0152489 A1 * | 6/2015 | Castro Signoret et al. | 435/5 |

FOREIGN PATENT DOCUMENTS

| | | |
|---|---|---|
| EP | 0435246 B1 | 8/1995 |
| EP | 2172774 A1 | 4/2010 |
| WO | 0005571 A1 | 2/2000 |

OTHER PUBLICATIONS

Noah et al. (Clinical and Vaccine Immunology, Apr. 2009, vol. 16, p. 558-566).*
Ellis et al. (Journal of Medical Microbiology, 2000, vol. 49. p. 853-859).*
Ananthanarayan, et al. Non-specific inhibitors of influenza viruses in normal sera. Bull World Health Organ. 1960;22:409-19.
Gottschalk. The chemistry and biology of sialic acids and related substances. Cambridge University Press, London.1960.
Lennette, et al. Haemagglutination Inhibition test. Diagnostic Procedures for viral, rickettsial and chlamydial infections. 5th Edition, American Public Health Association. 1979. 603.
Varki, et al. A neuraminidase from Streptococcus sanguis that can release O-acetylated sialic acids. J Biol Chem. Oct. 25, 1983;258(20):12465-71.
McHugh, TM et al. Simultaneous Detection of Antibodies to Cytomegalovirus and Herpes Simplex Virus by Using Flow Cytometry and a Microsphere-Based Fluorescence Immunoassay. Oct. 1988. Journal of Clinical Microbiology, vol. 26, No. 10, pp. 1957-1961; abstract; p. 1957, left column, second paragraph, DOI: 0095-1137/88/101957-05$02.00/0.
The International Search Report and the Written Opinion dated Mar. 13, 2014 for Application No. PCT/US13/51165.
Khare et al. A quantitative method for measuring nanocomposite dispersion. Polymer, Elsevier Science Publishers B. V, GB, vol. 51, No. 3, Feb. 5, 2010, pp. 719-729.
Li et al. Sensitive Imaging of H5N2 Virus by Self-Assembly Aggregation Molecular Switches. Nano-and Micro-Materials for Molecular Imaging. Sep. 7, 2011, abstract.
Lin et al. Synergistic Targeting-Imaging Approaches for Sensitive Virus and Tumor Detections. 20th Annual Meeting & Exhibition vol. 290, May 10, 2012.

(Continued)

*Primary Examiner* — Agnieszka Boesen

(57) ABSTRACT

Methods, compositions, systems, and devices are provided for performing and analyzing agglutination assays. In one aspect, methods for image analysis of agglutination assays are provided. In another aspects, methods for performing agglutination assays are provided. In one aspect, the methods may be used for the detection of various molecules, including viruses or antibodies against a virus. In another aspect, the methods can be used to determine effective immunization of a subject.

20 Claims, 14 Drawing Sheets

(56) References Cited

OTHER PUBLICATIONS

Meegen et al. Comparison of the latex agglutination test with the hemagglutination inhibition test, enzyme-linked immunosorbent assay, and neutralization test for detection of antibodies to rubella virus. Journal of Clinical Microbiology. vol. 16, No. 4, Oct. 1, 1982, pp. 644-649.

Ohmit et al. Influenza Hemagglutination-Inhibition Antibody Titer as a Correlate of Vaccine-Induced Protection. Journal of Infectious Diseases. JID, vol. 204, No. 12, Oct. 12, 2011, pp. 1879-1885.

Wiklund et al. Fluorescence-microscopy-based image analysis for analyte-depedent particle doublet detection in a single-step immunoagglutination assay. Analytical Biochemistry, Academic Press Inc, New York, vol. 338, No. 1, Mar. 1, 2005.

* cited by examiner

Agglutinated  Unagglutinated

A
B
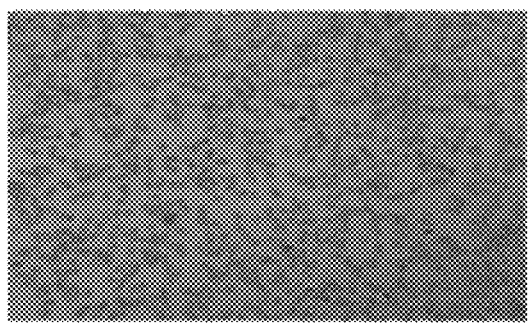 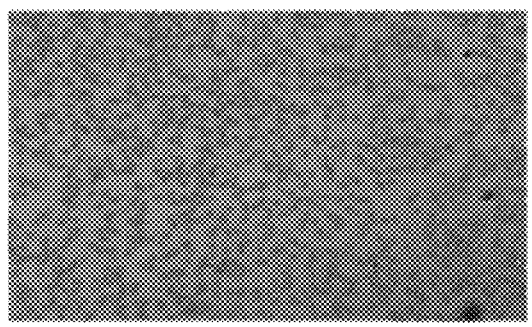
Fig. 12 A                                                    Fig. 12B A
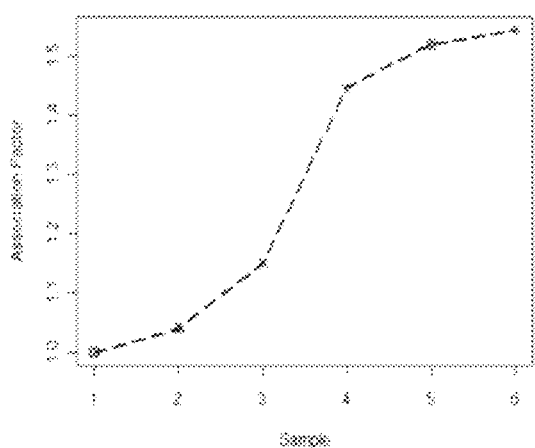
B
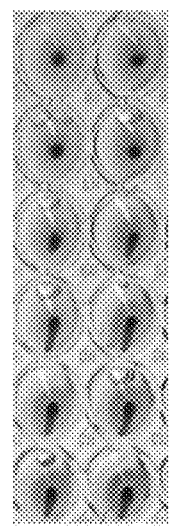
Fig. 14 A
Fig. 14 B

METHODS FOR DETECTING AND MEASURING AGGREGATION

CROSS REFERENCE

This application claims the benefit of U.S. Provisional Application No. 61/673,215 filed Jul. 18, 2012, which application is incorporated herein by reference in its entirety.

BACKGROUND

Aggregation or agglutination of molecules or cells forms the basis of various useful biological assays. Hemagglutination, or haemagglutination, is a specific form of agglutination that involves red blood cells (RBCs). This phenomenon is used in the laboratory to determine blood type, the presence and/or quantity of virus in a blood sample, and/or the quantity of certain anti-infectious agent antibodies. Hemagglutination causes RBCs to form macroscopic lattice structures that are stable against moderate agitation. These structures can be distinguished from non-agglutinated RBCs by visual observation, which forms the basis of a variety of traditional assay methods.

Hemagglutination can be triggered by viruses, bacteria, antibodies, and other factors (e.g. lectins). For example, antibodies that bind to type A antigens will induce hemagglutination in samples containing type A or AB RBCs. Similarly, viruses and viral antigens that bind to cell surface molecules can induce hemagglutination. Viruses may contain the protein "hemagglutinin", which binds to molecules on host cells. For example, hemagglutinin proteins may bind to sialic acid on the membrane of host cells such as RBCs. Viral titer can be approximated by observing hemagglutination at various dilutions of a sample containing virus. Bacteria can also be detected and quantified with these methods.

Despite the highly useful applications of hemagglutination assays, current methods are relatively slow, subjective, and unreliable for some purposes. Traditional pre-treatment protocols can take as long as 12-24 hours, and visual inspection is not a robust method for making quantitative determinations. Hemagglutination assays are often conducted in settings where time is of the essence (e.g. to prevent spread of a viral outbreak or during an emergency blood transfusion). Therefore, there is a considerable need in the art for improved methods of detecting and measuring aggregation/agglutination.

SUMMARY

Methods, compositions, systems and devices for improved agglutination assays are provided. In one aspect, improved imaging techniques for analysis of agglutination reactions are provided. In another aspect, methods for reducing the time and/or increasing the accuracy of agglutination reactions are provided. In another aspect, improved reagents for agglutination reactions are provided. In another aspect, improved devices for performing or analyzing agglutination reactions are provided. Additional improvements are also provided and the disclosure includes additional aspects. Multiple improvements disclosed herein may be used together.

In one aspect, a method for determining the presence of an antibody in a biological sample is provided, wherein the antibody binds selectively to a viral particle, and the method includes the steps of: (a) incubating a mixture of erythrocytes, the viral particle and the biological sample suspected of containing the antibody, under conditions permitting agglutination of the erythrocytes via interaction with the viral particle; and (b) detecting whether agglutination occurs in the mixture, wherein the absence of agglutination indicates the presence of the antibody, and wherein said steps (a)-(b) take place in less than one hour. In another related but separate aspect, the method includes (a) incubating a mixture of erythrocytes, a viral particle, and a biological sample suspected of containing the antibody, under conditions permitting agglutination of the erythrocytes via interaction with the viral particle; and (b) capturing with the aid of an optical device an image of the mixture, wherein the presence of an erythrocyte-viral particle cluster in the image indicates the occurrence of agglutination and lack of detectable amount of the antibody, and wherein the absence of the cluster indicates the lack of agglutination and the presence of a detectable amount of the antibody. In some embodiments, a microscopic image of the mixture is obtained.

In another aspect, a method for determining the presence of a viral particle in a biological sample is provided, wherein the method includes: (a) incubating a mixture of erythrocytes or modified red blood cells, a biological sample suspected of containing the viral particle, under conditions permitting agglutination of the erythrocytes via interaction with the viral particle; and (b) detecting whether agglutination occurs in the mixture, wherein the presence of agglutination indicates the presence of the viral particle, and wherein steps (a)-(b) take place in less than one hour. In a related but separate aspect, the method of determining the presence of a viral particle in a biological sample includes: (a) incubating a mixture of erythrocytes, a biological sample suspected of containing the viral particle, under conditions permitting agglutination of the erythrocytes via interaction with the viral particle; and (b) capturing with the aid of an optical device an image of the mixture, wherein the presence of an erythrocyte-viral particle cluster in the image indicates the occurrence of agglutination and the presence of detectable amount of the viral particle, and wherein the absence of the cluster indicates the lack of agglutination and the lack of detectable amount of the viral particle. In some embodiments, a microscopic image of the mixture is obtained.

In another aspect, a method for determining the effective immunization of a subject is provided, including: (a) obtaining a biological sample from a subject who has been immunized with a first dosage of a first vaccine against a viral particle; (b) incubating a mixture of erythrocytes, the viral particle, and the biological sample, under conditions permitting agglutination of the erythrocytes via interaction with the viral particle; and (c) determining the concentration of an antibody against the virus in the sample based on the clusters formed by the agglutination of the erythrocytes, and wherein said steps (b)-(c) take place in less than one hour. In a related but separate aspect, the method includes (a) obtaining a biological sample from a subject that has been immunized with a first dosage of a first vaccine against a viral particle; (b) incubating a mixture of erythrocytes, the viral particle, and the biological sample, under conditions permitting agglutination of the erythrocytes via interaction with the viral particle; (c) capturing with the aid of an optical device an image of the mixture; and (d) determining the concentration of an antibody against the viral particle in said biological sample based on the clusters formed by the agglutination of the erythrocytes, wherein the presence of an erythrocyte-viral particle cluster in the image indicates the occurrence of agglutination and lack of detectable amount of the antibody, and wherein the absence of the cluster indicates the lack of agglutination and the presence of detectable amount of the antibody. In some embodiments, a microscopic image of the mixture is obtained.

In one aspect, provided herein is a method for determining the presence of an antibody in a biological sample, wherein said antibody binds selectively to a viral particle, the method comprising: (a) incubating a mixture of erythrocytes, the viral particle, and the biological sample suspected of containing said antibody, under conditions permitting agglutination of the erythrocytes via interaction with said viral particle; (b) concurrent with or subsequent to (a), providing the mixture in a vessel having an opening at the top of the vessel and interior conical shape at the bottom of the vessel; (c) tilting the vessel such that after tilting, at least a portion of the mixture is closer to the opening at the top of the vessel than prior to the tilting, and wherein at least a portion of the sample remains in the vessel after the tilting; and (d) capturing with the aid of an optical device an image of said mixture, wherein the position of erythrocytes within the tilted vessel may be used to determine the presence or amount of said antibody in the sample.

In another aspect, provided herein is a method for determining the presence of a viral particle in a biological sample, wherein said viral particle may be selectively bound by an antibody, the method comprising: (a) incubating a mixture of erythrocytes, the antibody, and the biological sample suspected of containing said viral particle, under conditions permitting agglutination of the erythrocytes via interaction with said viral particle; (b) concurrent with or subsequent to (a), providing the mixture in a vessel having an opening at the top of the vessel and interior conical shape at the bottom of the vessel; (c) tilting the vessel such that after tilting, at least a portion of the mixture is closer to the opening at the top of the vessel than prior to the tilting, and wherein at least a portion of the sample remains in the vessel after the tilting; and (d) capturing with the aid of an optical device an image of said mixture, wherein the position of erythrocytes within the tilted vessel may be used to determine the presence or amount of said viral particle in the sample.

In another aspect, provided herein is a method for determining the presence of an antibody in a biological sample, wherein said antibody binds selectively to an agglutinating particle, the method comprising: (a) incubating a mixture of visualization particles, the agglutinating particle, and the biological sample suspected of containing said antibody, under conditions permitting agglutination of the visualization particle via interaction with said agglutinating particle; and (b) detecting whether said agglutination occurs in said mixture, wherein the absence of said agglutination indicates the presence of said antibody, wherein said steps (a)-(b) take place in less than one hour.

In another aspect, provided herein is a method for determining the presence of an antibody in a biological sample, where said antibody binds selectively to an agglutinating particle, the method comprising: (a) incubating a mixture of visualization particles, the agglutinating particle, and the biological sample suspected of containing said antibody, under conditions permitting agglutination of the visualization particle via interaction with said agglutinating particle; and (b) capturing with the aid of an optical device an image of said mixture, wherein the presence of a visualization particle-agglutinating particle cluster in said image indicates the occurrence of said agglutination and lack of detectable amount of said antibody, and wherein the absence of said cluster indicates the lack of said agglutination and the presence of detectable amount of said antibody.

In another aspect, provided herein is a method for determining the presence of an agglutinating particle in a biological sample, comprising: (a) incubating a mixture of visualization particles and a biological sample suspected of containing said agglutinating particle, under conditions permitting agglutination of the visualization particle via interaction with said agglutinating particle; and (b) detecting whether said agglutination occurs in said mixture, wherein the presence of said agglutination indicates the presence of said agglutinating particle, and wherein steps (a)-(b) take place in less than one hour.

In another aspect, provided herein is a method for determining the presence of an agglutinating particle in a biological sample, comprising: (a) incubating a mixture of visualization particles and a biological sample suspected of containing said agglutinating particle, under conditions permitting agglutination of the visualization particle via interaction with said agglutinating particle; and (b) capturing with the aid of an optical device an image of said mixture, wherein the presence of an visualization particle-agglutinating particle cluster in said image indicates the occurrence of said agglutination and the presence of detectable amount of said agglutinating particle, and wherein the absence of said cluster indicates the lack of said agglutination and the lack of detectable amount of said agglutinating particle.

In another aspect, provided herein is a method of determining the effective immunization of a subject, comprising: (a) obtaining a biological sample from a subject that has been immunized with a first dosage of a first vaccine against an agglutinating particle; (b) incubating a mixture of visualization particles, the agglutinating particle, and said biological sample, under conditions permitting agglutination of the visualization particles via interaction with said agglutinating particles; and (c) determining the concentration of an antibody against said agglutinating particle in said sample based on the clusters formed by the agglutination of the visualization particles, and wherein said steps (b)-(c) take place in less than one hour.

In another aspect, provided herein is a method of determining the effective immunization of a subject, comprising: (a) obtaining a biological sample from a subject that has been immunized with a first dosage of a first vaccine against an agglutinating particle; (b) incubating a mixture of visualization particles, said agglutinating particle, and said biological sample, under conditions permitting agglutination of the visualization particles via interaction with said agglutinating particle; (c) capturing with the aid of an optical device an image of said mixture; and (d) determining the concentration of an antibody against said agglutinating particle in said biological sample based on the clusters formed by the agglutination of the visualization particles, wherein the presence of a visualization particle-agglutinating particle cluster in said image indicates the occurrence of said agglutination and lack of detectable amount of said antibody, and wherein the absence of said cluster indicates the lack of said agglutination and the presence of detectable amount of said antibody.

In another aspect, provided herein is a kit, comprising: visualization particles, an agglutinating particle, and instructions for a user to use said kit for antibody or agglutinating particle detection.

In another aspect, provided herein is a method for determining the presence of an antibody in a biological sample, wherein said antibody binds selectively to an agglutinating particle, the method comprising: (a) incubating a mixture of visualization particles, the agglutinating particle, and the biological sample suspected of containing said antibody, under conditions permitting agglutination of the visualization particle via interaction with said agglutinating particle; (b) concurrent with or subsequent to (a), providing the mixture in a vessel having an opening at the top of the vessel and interior conical shape at the bottom of the vessel; (c) tilting the vessel such that after tilting, at least a portion of the mixture is closer to the opening at the top of the vessel than prior to the tilting, and wherein at least a portion of the sample remains in the vessel after the tilting; and (d) capturing with the aid of an optical device an image of said mixture, wherein the position of visualization particles within the tilted vessel may be used to determine the presence or amount of said antibody in the sample.

In another aspect, provided herein is a method for determining the presence of an agglutinating particle in a biological sample, wherein the agglutinating particle may be selectively bound by an antibody, the method comprising: (a) incubating a mixture of visualization particle, the antibody, and the biological sample suspected of containing said agglutinating particle, under conditions permitting agglutination of the visualization particles via interaction with said agglutinating particle; (b) concurrent with or subsequent to (a), providing the mixture in a vessel having an opening at the top of the vessel and interior conical shape at the bottom of the vessel; (c) tilting the vessel such that after tilting, at least a portion of the mixture is closer to the opening at the top of the vessel than prior to the tilting, and wherein at least a portion of the sample remains in the vessel after the tilting; and (d) capturing with the aid of an optical device an image of said mixture, wherein the position of visualization particles within the tilted vessel may be used to determine the presence or amount of said agglutinating particle in the sample.

In practicing any of the subject methods, the erythrocytes can be pre-fixed, e.g., by treatment with glutaraldehyde. Where desired, the erythrocytes may include turkey red blood cells or red cells from other non-human RBCs.

The viral particles detected by any of the subject methods can include any type of agglutinating virus. For example and without limitation, hepatitis B virus (HBV), hepatitis C virus (HCV), and any strain of influenza virus may be detected by methods disclosed herein. In some aspects, antibodies detected by any of the methods disclosed herein can be against any type of agglutinating particle, such as agglutinating viruses. For example and without limitation, antibodies against HBV, HCV and any strains of influenza virus may be detected.

The biological sample utilized in any of the methods disclosed herein can be any suitable bodily fluid, processed or unprocessed, including but not limited to fresh or anti-coagulated whole blood, plasma and serum. In some instances, the plasma or serum is from a subject that has been administered with a vaccine against the viral particle. Where desired, the biological sample can be pre-treated with neuraminidase, for example, by incubating said biological sample with neuraminidase, for a suitable period of time such as less than 2 hours, 1 hour, 30 minutes, 20 minutes, 10 minutes, 5 minutes or even less.

In some embodiments, the various steps employed in a method disclosed herein can be completed within about 2 hours, 60 minutes, 45 minutes, 30 minutes or less, or between about 30 to about 60 minutes.

In one aspect, provided herein are methods of analyzing agglutination based on image analysis. In one embodiment, image analysis methods are used to analyze the bulk movement of RBCs or visualization particles in an agglutination assay in a conical well or tube. In another embodiment, image analysis methods are used to analyze microscopic images of RBCs or visualization particles in suspension in an agglutination assay, in order to interrogate the fine structure of the RBC or visualization particle suspension.

In one aspect, provided herein are methods for image analysis of bulk movement of RBCs and visualization particles. In one embodiment, a method is provided for image analysis of agglutination reactions using designated locations in a reaction vessel (e.g. reaction tube or well). In one embodiment, a method is provided for image analysis of agglutination reactions using scanning of the packed cells of an agglutination reaction. In one embodiment, a method is provided for image analysis of agglutination reactions using determination of the area and/or perimeter of the packed cells an agglutination reaction. In some aspects, packed cells include a button and/or teardrop region.

In some embodiments, the presence of the agglutination is evidenced by formation of erythrocyte-viral particle clusters, and wherein said clusters are captured in an imaging region of an optical device. The optical device can include without limitation a camera, a microscope, an optical scanner, a sensor, a detector, or any other suitable imaging device. Where desired, an analysis of the agglutination reaction can be performed by calculating the size of said clusters based on the center-to-center distance of individual erythrocytes captured in each of said images.

In some embodiments, a method for determining the effective immunization of a subject, can further include the step of administering a second dosage of the first vaccine against the viral particle to the subject if the concentration of the antibody in the biological sample is lower than a predetermined level.

Further provided is a kit, including: pre-fixed erythrocytes, a viral particle, and instructions for a user to use the kit for antibody or viral detection. Such instructions may be wirelessly transmitted and executed in automated systems.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

In the drawings,

FIG. 6 depicts schematics related to analysis of bulk movement of visualization particles by image analysis at designated locations in a vessel.

FIG. 12 shows representative microscopic images for a non-aggregated sample as shown in FIG. 12A and an aggregated sample as shown in FIG. 12B.

FIG. 14B and FIG. 14C contain images of the samples analyzed in FIG. 14A and FIG. 14D, respectively. FIG. 14B and FIG. 14C show images of the pelleting assay using the method of plate tilting and observation of the flow characteristics of packed red cells. In panels FIG. 14B and FIG. 14C, the wells are numbered 1-6 from the bottom to the top, and the adjacent wells in each of the right and left row are duplicates of the same assay conditions.

DETAILED DESCRIPTION

Figure 1:
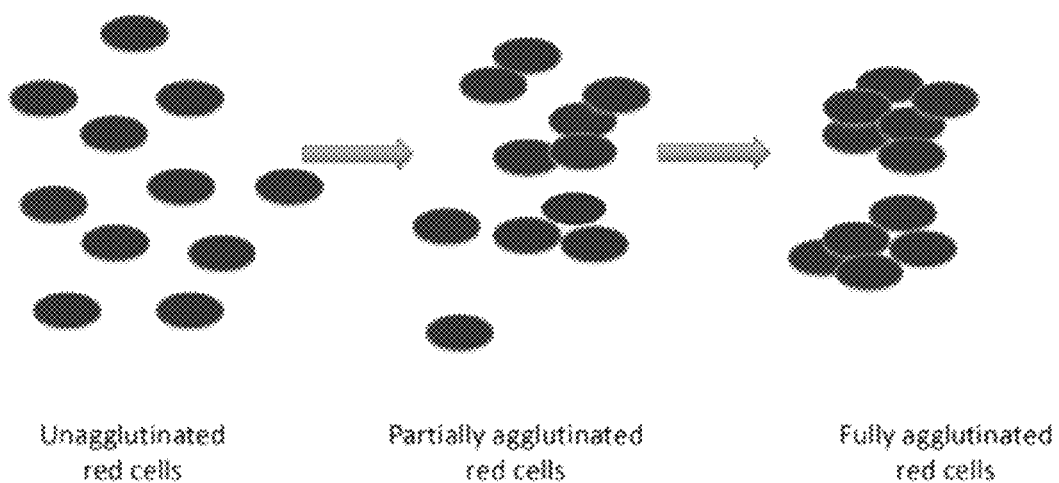
FIG. 1 depicts agglutination of red blood cells.

Provided herein are compositions, systems, devices, and methods related to assays for a viral particle, agglutinating particle, antigen or an antibody to an antigen in a sample, by detecting the occurrence of agglutination of erythrocytes or other particles which may be selectively agglutinated/aggregated, such as microspheres.

A. DEFINITIONS

The articles "a", "an" and "the" are non-limiting. For example, "the method" includes the broadest definition of the meaning of the phrase, which can be more than one method.

A "subject" may be a human or animal. The subject may be living or dead. The subject may be a patient, clinical subject, or pre-clinical subject. A subject may be undergoing diagnosis, treatment, and/or disease prevention. The subject may or may not be under the care of a health care professional.

A "blood sample" is a sample of blood or any blood fraction, blood derivative and the like. Plasma is an example of a blood fraction. The blood sample can have any suitable volume, be obtained by any suitable method, be collected from any part of the subject at any time, be collected in any suitable vessel, and the like. Blood is a specialized bodily fluid in animals (including humans) that delivers necessary substances such as nutrients and oxygen to the cells and transports metabolic waste products away from those same cells. Blood samples may have any suitable materials added, optionally one or more anti-coagulants. "Blood sample" also includes blood samples that are diluted.

"Plasma" is the liquid component of blood. It is the intravascular fluid part of extracellular fluid (all body fluid outside of cells). It is mostly water (about 93% by volume) and may contain dissolved proteins, glucose, clotting factors, mineral ions, hormones and carbon dioxide (plasma being the main medium for excretory product transportation). Blood plasma may be prepared by spinning (centrifuging) a tube of blood containing an anti-coagulant in a centrifuge until the blood cells sediment to the bottom of the tube. The blood plasma is then aspirated or drawn off.

"Blood serum" is blood plasma without fibrin, fibrinogen or the other clotting factors (i.e., whole blood minus both cells and clotting factors).

Blood samples may be obtained by a "non-venous route", meaning that the blood is not drawn from the veins and arteries of the body with a needle. Non-venous route does not limit the blood sample to being either venous blood (deoxygenated blood) or arterial blood (oxygenated blood). Both venous blood and arterial blood are suitable. Obtaining blood from capillaries of the body is one example of a non-venous route.

A "finger prick", "fingerstick", or similar is one example of a method suitable for obtaining a blood sample by a non-venous route. Here, a sharp point or edge may be used to penetrate the skin of the finger (or any other part of the body), causing blood to emanate from the body. A fingerstick may also be performed on the heel, optionally on the heel of a baby, for example. The blood may be collected using a capillary tube, pipette, swab, drop, or any other mechanism known in the art.

By "agglutination", "aggregation", or grammatical equivalent thereof, herein means the process by which particles such as molecules or cells cluster in space over a course of time. The resulting aggregates have at least some different properties than the individual un-aggregated particles, and assays to detect or measure these aggregates provide useful information.

The term "viral particle" includes any molecule or material that contains a virus or viral components. The term includes whole viruses, as well as parts of viruses. Viral particles include viral antigens. Viral antigens include, without limitation, viral polypeptides, nucleic acids, and carbohydrates.

The term "erythrocyte" includes any form of a red blood cell, from any organism. Thus, the term includes fresh, unaltered, red blood cells, as well as red blood cells that have been subjected to a chemical or other treatment. The term includes red blood cells from mammals, birds, reptiles, amphibians, fish, invertebrates, or any other type of organism.

"Images" are any artifact, for example a two-dimensional picture, set of pictures, or video that has a similar appearance to some physical object. Images may involve the capture of light by a camera.

Images may be "pixilated", meaning that they comprise pixels.

A "point of service" is any location that may receive or analyze a sample from a subject, any location where the health of a subject may be monitored, any location where a subject may receive a medical treatment, or any location where a subject may receive an answer or resolution to a health-related question or issue. In some embodiments, a point of service is a subject's location (e.g., home, business, sports event, security screening, combat location), the location of a healthcare provider (e.g., doctor), a pharmacy, a retailer, a clinic, a hospital, an emergency room, a nursing home, a hospice care location, or a laboratory. A retailer may be, for example, a pharmacy (e.g., retail pharmacy, clinical pharmacy, hospital pharmacy), drugstore, chain store, supermarket, or grocer. In some situations, a point of service is any location that is designated for use by a certifying or licensing entity (e.g., a government certifying entity). In other situations, a point of service a transportation vehicle, such as a car, boat, truck, bus, airplane, motorcycle, van, traveling medical vehicle, mobile unit, ambulance, fire engine/truck, critical care vehicle, or other vehicle configured to transport a subject from one point to another. In some embodiments, a point of service is a "point of care." A "point of care" is a point of service where a subject may receive medical treatment. A "point of care" can include any location at or near the site where a subject may receive medical treatment, including, without limitation, hospitals, doctor's offices, transportation vehicles, or a subject's home. A "point of care" can include locations such as grocery stores, pharmacies, or businesses, if such locations are configured to provide any form of medical treatment, and/or are configured to host medical personnel that provide medical treatment to a subject.

"Video" images are a series of images collected sequentially over time. Video images may be collected at any rate, including for example, at at least 1 frame/minute, at least 1 frame/10 seconds, at least 1 frame/second, at least 10 frames/second, at least 20 frames/second, at least 30 frames/second, at least 40 frames/second, at least 50 frames/second, at least 100 frames/second, or at least 200 frames/second.

B. GENERAL CONSIDERATION

Hemagglutination assays have been in use for many years with complex, slow protocols. The character of the agglutination reaction is that large structures are held together by relatively weak forces (non-covalent protein-protein interactions). Such processes respond to mechanical forces like agitation and mixing of the cell suspension. The character of the agglutinates is dependent not only on the reactants but also on the shape of the vessel in which the reaction occurs. The temperature, solvent composition, presence of polymers such as proteins, carbohydrates (e.g. Dextran) and other (e.g. poly-ethylene glycol) polymers all have effects on the reaction. A general schematic of an agglutination reaction is shown in FIG. 1.

To read agglutination reactions, several optical methods are currently used.

Figure 2:
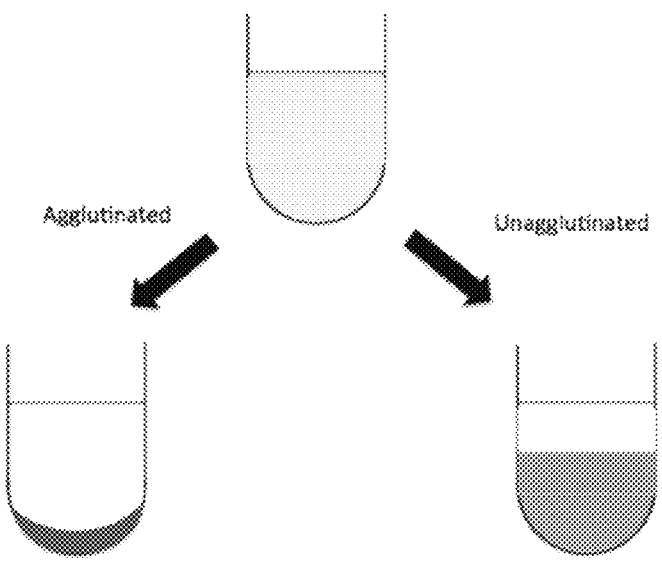
FIG. 2 illustrates the traditional pelleting assay by which agglutinated and non-agglutinated samples can be distinguished.

In the first method, shown in FIG. 2, the reaction vessel is a straight-sided circular tube. Agglutinated red cells settle more quickly than unagglutinated cells. After sufficient time has passed, the agglutinated cell reaction product exhibits a clear supernatant with a pellet of agglutinated cells, while the unagglutinated cell reaction remains turbid, with the unagglutinated cells remaining in suspension.

Figure 3:
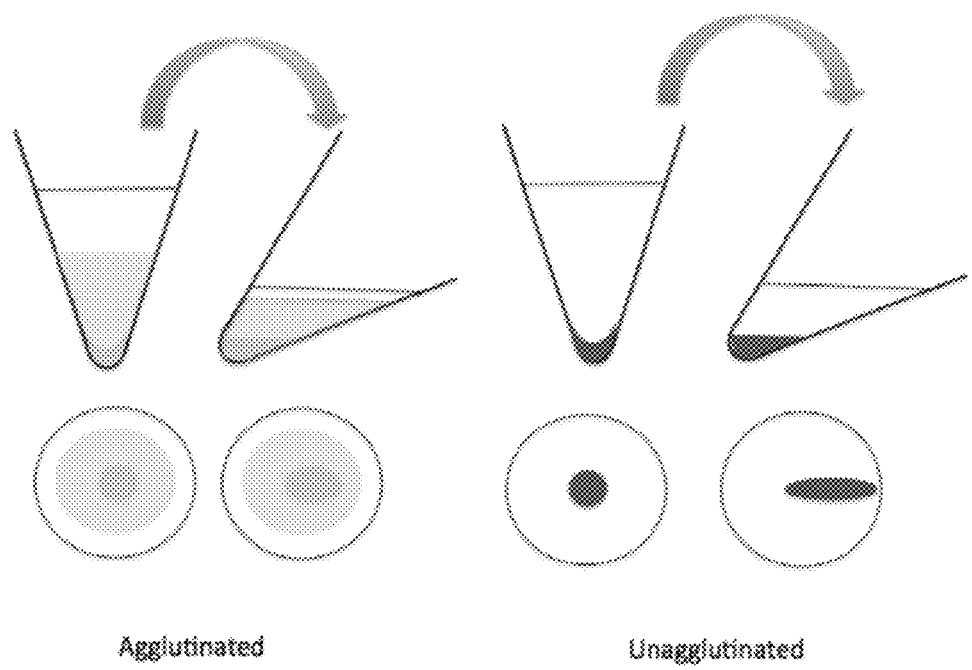
FIG. 3 illustrates the traditional pelleting assay by which agglutinated and non-agglutinated samples can be distinguished in conical tubes.

The second method is illustrated in FIG. 3. It has been found that using conical tubes can cause some agglutinated red blood cells to form a distributed lattice/mat at the bottom of the tube, while some of the agglutinated red blood cells remain suspended in solution. In contrast, most of the unagglutinated cells roll down the sides of the tube to form a "button" at the narrow bottom tip of the tube, but this button is loosely packed. In order to help identify whether cells in conical tubes are agglutinated or unagglutinated after an agglutination assay, conical tubes may be tilted after the cells have been given sufficient time to settle in the assay. When such tubes are tilted at an angle as in FIG. 3, the button of unagglutinated cells flows to form a "teardrop" shaped mass, whereas agglutinated cells exhibit significantly less flow.

The methods, compositions, systems and devices provided herein for agglutination assays have multiple advantages over existing technologies.

In one aspect, a method is provided for determining the presence of a viral particle using a binding assay. As provided in more detail herein, in one aspect, in this assay, the viral particle, if present, binds to erythrocytes and forms erythrocyte-viral particle clusters, and accordingly leads to agglutination. This may be referred to as a hemagglutination assay (HA). See FIG. 4, panel A.

In a further aspect, a method is provided for determining the presence of an antibody using a binding assay. As provided in more detail herein, in one aspect, in this assay, the antibody, if present, binds to the erythrocytes and forms erythrocyte-viral particle clusters, and accordingly leads to agglutination. This also may be referred to as a hemagglutination assay (HA). See FIG. 4, panel B.

In one aspect, a method is provided for determining the presence of antibody using a competition assay. As provided in more detail herein, in one aspect, in this assay the antibody, if present, binds to the surface of a viral particle, thus preventing the viral particle from binding to the erythrocytes and forming erythrocyte-viral particle clusters. Thus, the antibody against the viral particle results in the absence or inhibition of agglutination. This may be referred to as a hemagglutination assay inhibition (HAI) See FIG. 5.

In one aspect, methods provided herein may reduce the sample pre-treatment time for agglutination assays to as little as 30 minutes or less. In one aspect, this may be achieved by the use of neuraminidase during sample pre-treatment.

In another aspect, methods provided herein may simplify the hemagglutination assay reagent set. For example, in some embodiments the methods provided herein employ a single, stable type of red blood cell preparation (or its equivalent, such as microsphere) for all hemagglutination assays. An example of a stable type of red cell preparation is turkey red cells stabilized by glutaraldehyde fixation. Such fixed cells are essentially indefinitely stable (in contrast to fresh red cells which have to be prepared daily and will vary from day to day). Fixation does not inactivate the cell surface receptors to which the viral hemagglutinin or other agglutinating particles bind. Fresh red cells and cells from different animal species can also be used in the disclosed methods.

In some aspects, methods of the present disclosure include the combination of assay steps. While the traditional HAI method uses at least two separate incubations (one reaction of treated sample containing antibodies with viral antigen, plus one reaction with red cells, totaling about 60 minutes), the methods provided herein for may use of a single incubation. Such incubation may be significantly shorter than in traditional methods, such as taking about 45 minutes, about 30 minutes, about 25 minutes, about 20 minutes, about 15 minutes, about 10 minutes, about 5 minutes, about 4 minutes, about 3 minutes, about 2 minutes, or about 1 minute. In certain embodiments, two steps can also be used.

In some aspects, methods of the present disclosure accelerate agglutination reactions. Agglutination reactions are sensitive to the assay medium composition. Charge-charge interactions and weak interactions with, for example, polymers (proteins, carbohydrate polymers such as dextran) and the like all may have profound effects on the agglutination rate and end-point. In some embodiments, with glutaraldehyde-fixed turkey red cells, albumin can accelerate the agglutination reaction by about four fold.

Methods of the present disclosure further provide objective analysis of the agglutination end-point. Image analysis can be used to read hemagglutination assays objectively and quantitatively without the need for titration of sample. Certain methods for image analysis are provided in U.S. Provisional Appl. No. 61/435,250, filed Jan. 21, 2011, which is hereby incorporated by reference in its entirety.

In one embodiment, a digital image of an agglutination assay in a conical tube reaction container is collected. This image can be interpreted to measure the extent of "teardrop" formation (length of red cell column). In another embodiment, "cluster analysis" of visualization particles may be performed as described in detail below. This method enables an agglutination reaction to be read after very short time.

Furthermore, the methods provided herein may reduce total agglutination assay time. Table 1 provides a comparison of the traditional method and an exemplary embodiment of the methods provided herein. As shown in Table 1 below, the methods provided herein may result in a more than 20-fold reduction in assay time and a significant reduction in agglutination assay protocol complexity.

TABLE 1

| | Time (hours) | |
| --- | --- | --- |
| Step | Traditional method | Exemplary embodiment of present method |
| Red cell reagent preparation | 4 | n/a |
| Sample pre-treatment | 18 | 0.5 |
| Inactivation of pre-treatment reagent | 0.5 | 0.1 |
| Incubation with viral antigen | 0.5 | 0.3 |
| Incubation with red cell reagent | 0.8 | |
| Total time | 24 | 0.9 |
| Steps | 6 | 4 |

Methods disclosed herein can further eliminate of the need for serial dilution of reagents by use of an objective, kinetic readout.

II. Agglutination Assays

A. Hemagglutination Assay (HA Assay)

In one aspect, provided herein are methods, compositions, devices, and systems relating to hemagglutination assays (HA). Hemagglutination assays may be used as a method of detection or quantification for viruses, bacteria, antibodies or other hemagglutinating particles by hemagglutination.

Agglutination of erythrocytes can be referred to as hemagglutination

As used herein, the term "visualization particle" refers to any cell or particle that may be agglutinated and detected macroscopically or microscopically. "Visualization particles" include, without limitation, erythrocytes, other cells, and microspheres.

As used herein, the term "agglutinating particle" refers to any molecule or organism which may bind to and cause aggregation of cells or visualization particles. "Agglutinating particles" include, without limitation, viruses, viral particles, and antibodies.

In some aspects, any of the assays described herein as "hemagglutination assays" or "hemagglutination inhibition assays" may also be carried out with non-red blood cell visualization particles (e.g. microspheres, bacteria) functioning in the role of RBCs in an HA or HAI assay, and appropriate corresponding agglutinating particles. Furthermore, an HAI may be performed to assay for any antibody that can bind to any agglutinating particle, in order to inhibit the agglutination of visualization particles by that agglutinating particle.

Figure 4:
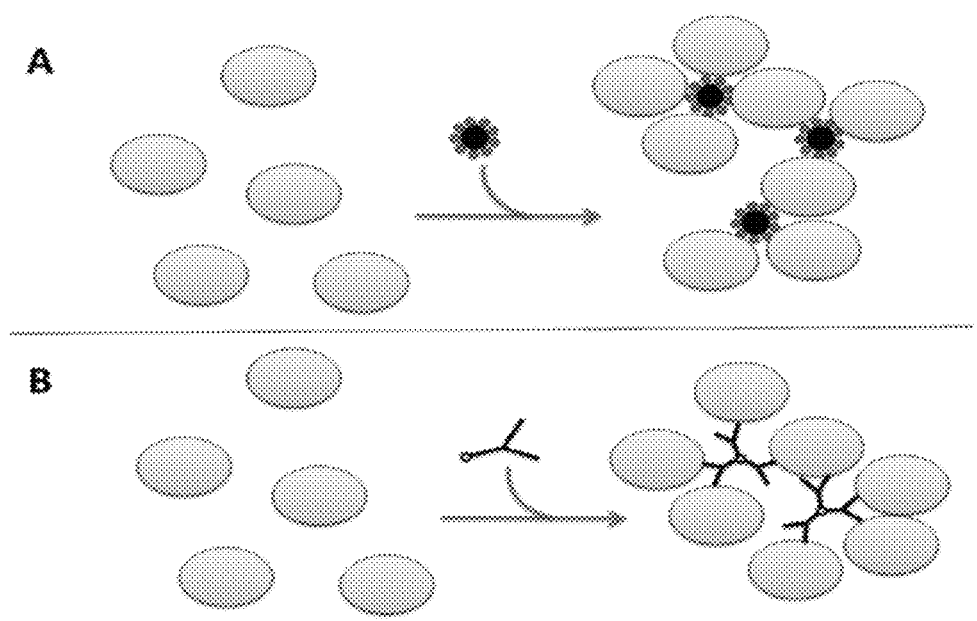
FIG. 4 depicts (FIG. 4A) virus-mediated aggregation of cells and (FIG. 4B) antibody-mediated aggregation of cells.

In one aspect, provided herein are improved methods of detecting and measuring hemagglutination, as well as improved methods of detecting and measuring inhibition of hemagglutination. Assays for detecting or measuring hemagglutination can be referred to as HA assays. Assays for detecting or measuring inhibition of hemagglutination can be referred to as HAI assays. FIG. 4 illustrates the process of hemagglutination induced by A) virus and B) antibody. Virus-induced hemagglutination can be used, for example, to detect the presence of or quantify an amount of a virus or viral particle, also known as viral titer. Antibody-induced agglutination can be used, for example, to determine blood type of erythrocytes in a sample.

In one embodiment, provided herein is a method for determining the presence of a viral particle in a biological sample, including: (a) incubating a mixture of erythrocytes and a biological sample suspected of containing the viral particle, under conditions permitting agglutination of the erythrocytes via interaction with the viral particle; and (b) detecting whether agglutination occurs in the mixture, wherein the presence of agglutination indicates the presence of the viral particle, and wherein steps (a)-(b) take place in less than one hour. The detection and analysis of agglutination is carried out as provided herein.

In another aspect, provided herein is a method for determining the presence of an agglutinating particle in a biological sample, including: (a) incubating a mixture of visualization particles and a biological sample suspected of containing the agglutinating particle, under conditions permitting agglutination of the visualization particle via interaction with the agglutinating particle; and (b) detecting whether said agglutination occurs in said mixture, wherein the presence of said agglutination indicates the presence of said agglutinating particle, and wherein steps (a)-(b) take place in less than one hour. The detection and analysis of agglutination is carried out as provided herein.

Detection of agglutination generally involves taking images of the agglutination using an imaging device, such as a scanner, camera, detector, or sensor, coupled to a microscope.

In general, the assay is carried using a device that is capable of holding the reactions, such as a 96-well microtiter plate or its equivalent. A pre-treated biological sample containing the viral particle or hemagglutinating particle to be detected may be serially diluted in the plate with a diluent buffer (e.g. PBS with BSA). Then, pre-fixed RBCs or visualization particles in suspension may be added, followed by gentle mixing. The reaction is incubated for a suitable period of time, for example, a total of about 15 minutes. However, a total incubation shorter or longer than 15 minutes may also be used, such as about 10 or 5 minutes or shorter, or 20, 25, 30, 35, 40, 50, 60 minutes, or longer. The incubation may be carried at room temperature (i.e., 25° C.), or at a temperature that is lower or higher than room temperature, such as about 4, 8, 12, 14, 16, 20, 30, 35, 40, 45, 50, 55, 60, 65, or 70° C. The temperature and duration of incubation can be optimized to achieve both speed and accuracy of the assays. The plate may be read on a scanner and a final end-point image is taken of the plate, preferably when the plate is tilted at 20-75°, such as at about 20, 25, 30, 35, 40, 45, 50, 55, 60, 65, 70, or 75°.

In some embodiments, an image of the agglutination is captured with an optical device which includes a microscope. In these embodiments, the assay is generally carried as described above, except after the pre-fixed RBCs or visualization particles are added to the reaction, a small sample (e.g. 1-2 µL) from the wells is transferred directly into a cuvette or tip, and imaged under an optical device containing a microscope. Images are collected and analyzed to calculate association factors as described in more detail herein.

The duration for performing the agglutination assay is generally optimized to achieve both speed and accuracy of the assay. In some embodiments, performing the assay and detecting agglutination takes place in less than one hour, such as about 10, 15, 20, 30, 40, 50, or 60 minutes. In some embodiments, performing the assay and detecting agglutination takes place in more than one hour, but less than 2, 3, 4, 5, 6, 7, or 8 hours.

In some embodiments, an HA assay is performed using a sample known not to contain an agglutinating virus, to ensure that observed agglutination is a result of agglutinating virus or agglutinating particle (i.e. a negative control). In some embodiments, an HA assay is performed using a sample known to contain an agglutinating virus, to ensure that erythrocytes or visualization particles used in the assay are capable of undergoing agglutination (i.e. a positive control).

B. Hemagglutination Inhibition Assay (HAI Assay)

In one aspect, provided herein are methods, compositions, devices, and systems relating to hemagglutination inhibition assays (HAI). Hemagglutination inhibition assays measure the ability of a sample to inhibit hemagglutination. HAI assays are useful, for example, for detecting or measuring the presence of antibodies capable of binding an agglutinating virus or an agglutinating particle and inhibiting its ability to agglutinate. The presence of such binding can be a useful indicator of the presence of antibodies against a virus or agglutinating particle.

Figure 5:
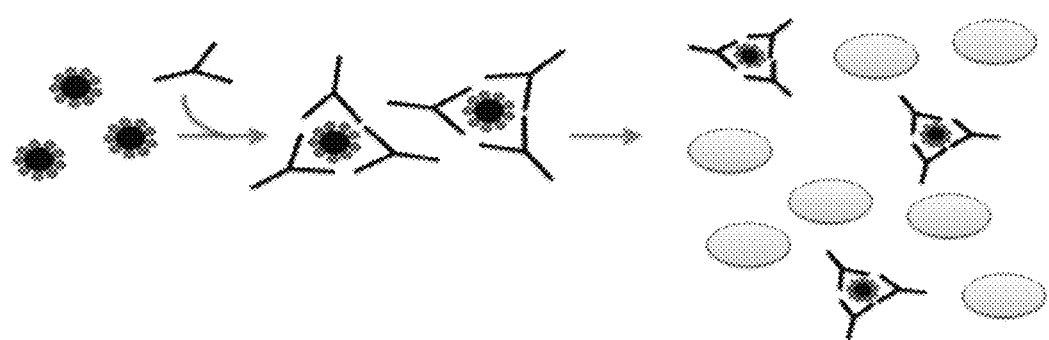
FIG. 5 depicts antibody-mediated inhibition of virus-mediated aggregation of cells.

Referring to FIG. 5, a schematic diagram of inhibition of hemagglutination is depicted. In some embodiments, a reagent containing virus is incubated with a sample that may contain antibodies that bind selectively to the virus. Antibody binding to a viral particle can interfere with the viral particle's ability to induce hemagglutination. Inhibition of hemagglutination thus serves to indicate the presence of antibody. In this way, HAI assays may be used to detect or measure antibodies in a biological sample.

In the traditional approach, the HAI assay is performed in at least three steps: (1) pre-treatment of sample suspected of containing an antibody; (2) incubation of pre-treated sample suspected of containing an antibody with a virus (antibodies to the virus bind to the hemagglutinin on the viral particles, rendering the hemagglutinin inactive) for up to 24 hours; and (3) the material from step (2) is inactivated, and then a preparation of red cells (freshly made) is added, and the mixture incubated for a total of about 2 hours.

In some embodiments, methods of the disclosure improve on the traditional method by removing the need for three separate steps. In some embodiments, reagent red blood cells and viral antigens are combined into a single reagent. In some embodiments, agglutinating particles and visualization particles are combined into a single reagent.

B1. Detection of Antibodies

In one aspect, a method for determining the presence of an antibody in a biological sample is provided, wherein the antibody binds selectively to a viral particle, and the method includes: (a) incubating a mixture of erythrocytes, the viral particle, and the biological sample suspected of containing said antibody, under conditions permitting agglutination of the erythrocytes via interaction with said viral particle; and (b) detecting whether agglutination occurs in the mixture, wherein the absence of agglutination indicates the presence of said antibody, and wherein said steps (a)-(b) take place in less than one hour. The detection and analysis of agglutination is carried out as provided herein.

In one aspect, a method for determining the presence of an antibody in a biological sample is provided, wherein the antibody binds selectively to an agglutinating particle, and the method includes: (a) incubating a mixture of visualization particles, the agglutinating particle, and the biological sample suspected of containing the antibody, under conditions permitting agglutination of the visualization particles via interaction with the agglutinating particle; and (b) detecting whether agglutination occurs in the mixture, wherein the absence of the agglutination indicates the presence of the antibody, and wherein the steps (a)-(b) take place in less than one hour. The detection and analysis of agglutination is carried out as provided herein.

In some embodiments, the viral particle and the biological sample are incubated together before adding the erythrocytes. In some embodiments, the agglutinating particle and the biological sample are incubated together before adding the visualization particles.

B2. Detection of Viral Particles or Hemagglutinating Particles

In another aspect, an HAI assay is used to detect or measure a specific viral particle or agglutinating particle. A sample suspected of containing a specific viral particle or agglutinating particle is assayed for agglutination, in the presence or absence of known, fixed quantities of (reagent) antibodies known to bind selectively to the specific viral particle or agglutinating particle. If the viral particle or agglutinating particle still induces agglutination in the presence of the antibodies, the sample does not contain (or only contains a low amount) the specific viral particle or agglutinating particle of interest. If, on the other hand, agglutination is observed to be inhibited by the presence of specific the antibodies, then the viral particle or agglutinating particle in the sample is a match for the specific virus or viral particle of interest.

In some embodiments, an HAI assay is performed without titration of the unknown quantity of virus or antibody. The objective analysis of the methods herein provide high sensitivity to even minute changes in the state if aggregation of RBCs. This high resolution reduces ambiguity in determining the exact transition point between agglutination/non-agglutination. This can eliminate the need for titration, greatly simplifying the assay protocol.

In some embodiments, an HAI assay is performed using a sample known not to contain an agglutinating virus or agglutinating particle, to ensure that agglutination is a result of agglutinating virus or agglutinating particle (i.e. a negative control). In some embodiments, an HAI assay is performed using a sample known to contain an agglutinating virus or agglutinating particle, but lacking antibodies, to ensure that erythrocytes or visualization particles used in the assay are capable of undergoing agglutination (i.e. a positive control). This control also helps to set a baseline measurement for agglutination from which antibody-induced inhibition can be determined.

C. BIOLOGICAL SAMPLES

In one aspect, provided herein are methods for determining the presence of an antibody, viral particle, antigen, or agglutinating particle in a biological sample.

By "biological sample" herein is meant a sample derived from a biological source. Examples of biological samples include but are not limited to, blood, serum, saliva, urine, gastric and digestive fluid, tears, stool, semen, vaginal fluid, interstitial fluids derived from tumor tissue, ocular fluids, bodily tissue, or spinal fluid. Examples of tissue samples of the subject may include but are not limited to, connective tissue, muscle tissue, nervous tissue, epithelial tissue, cartilage, or bone. The sample may be provided from a human or animal. The sample may be collected from a living or dead subject. The sample may be collected fresh from a subject or may have undergone some form of pre-processing, storage, or transport.

In some embodiments, the biological sample comprises plasma or serum derived from blood.

Methods for obtaining, preparing, handling, and storing blood and blood-derived samples (e.g., plasma, serum) are well known in the art and include those described in U.S. Pat. No. 7,901,873.

In some embodiments, the blood, plasma or serum is derived from a subject (e.g. a human) that has been administered with a vaccine against an antigen. The antigen may be, for example, a viral particle or agglutinating particle.

A subject may provide a sample, and/or the sample may be collected from a subject. A subject may be a human or animal. The subject may be living or dead. The subject may be a patient, clinical subject, or pre-clinical subject. A subject may be undergoing diagnosis, treatment, monitoring and/or disease prevention. The subject may or may not be under the care of a health care professional. The subject may be a person of any age, an infant, a toddler, an adult or an elderly.

Any volume of sample may be provided from the subject. Examples of volumes may include, but are not limited to, about 10 mL or less, 5 mL or less, 3 mL or less, 1 mL or less, 500 µL, or less, 400 µL, or less, 300 µL or less, 250 µL, or less, 200 µL, or less, 170 µL or less, 150 µL, or less, 125 µL, or less, 100 µL or less, 75 µL or less, 50 µL, or less, 25 µL, or less, 20 µL or less, 15 µL, or less, 10 µL or less, 9 µL or less, 8 µL, or less, 7 µL or less, 6 µL, or less, 5 µL or less, 4 µL or less, 3 µL or less, 2 µL, or less, 1 µL, or less, 750 nL or less, 500 nL or less, 250 nL or less, 100 nL or less, 50 nL or less, 20 nL or less, 10 nL or less, 5 nL or less, 1 nL or less, 500 pL or less, 100 pL or less, 50 pL or less, or 1 pL or less. The amount of sample may be about a drop of a sample. The amount of sample may be the amount collected from a non-venous route. The amount of sample may be the amount collected from a pricked finger or fingerstick. Any volume, including those described herein, may be used in the methods disclosed herein.

C1. Pretreatment of Biological Samples

In some embodiments, the biological sample is pre-treated, to reduce non-specific background.

Pre-treatment generally includes treatments to reduce background or false positive measurements associated with a biological sample. Blood serum and plasma frequently contain factors [in particular glycoproteins (also called "receptors") which are not antibodies to a virus] which bind to the viral hemagglutinin and cause inhibition of agglutination reactions. The main class of such glycoproteins have polysialic acid chains covalently linked to the protein. The presence of such proteins falsely elevates the measured antibody titer. To eliminate this problem the sample can be pre-treated to eliminate the interfering factors before running the hemagglutination assay. The hemagglutination reaction with influenza virus found by Hirst [G. K. Hirst, Science, vol. 94, 22 (1944)] suggested the presence of receptors for influenza virus on the cell membrane and the presence of hemagglutinin which recognizes and binds to the receptor, as well as the presence of receptor-destroying enzymes. Later, the receptor-destroying enzymes were found to be sialidases. The hemagglutinin and the sialidase are essential molecular species for establishment of infection and extracellular release of viruses such as adsorption to the receptor, destruction of the receptor, intracellular invasion associated with membrane fusion and liberation of the matured virus from the cell. Sialic acid-containing receptors can give rise to false positive measurements in HA and HAI assays. Therefore in some embodiments, a sample is pre-treated.

Two enzymes are generally used for sample pre-treatment to reduce background in agglutination reactions: (1) Receptor destroying enzyme ("RDE"), which cleaves sialic acid attached to glycoproteins or glycolipids, and (2) Neuraminidase which cleave exo or endo poly-sialic acids. The traditional pre-treatment method uses RDE for about 20 hours.

In some embodiments, the biological sample is pre-treated with neuraminidase. Neuraminidase refers to a class of enzymes that are glycoside hydrolase enzymes that cleave the glycosidic linkages of neuraminic acids. Neuraminidase enzymes are a large family of enzymes, which are found in a range of organisms, including viruses. Neuraminidases are also called sialidases for their ability to catalyze the hydrolysis of terminal sialic acid residues from proteins such as receptors. Major classes of neuraminidases include viral neuraminidase, bacterial neuraminidase, mammalian neuraminidases, lysosomal sialidase, cytosolic sialidase, and membrane sialidase.

In some embodiments, pre-treatment of a biological sample with a neuraminidase provides an advantage in reaction speed. In some embodiments, sample pre-treatment is carried out by incubating a sample with neuraminidase for less than 30 minutes.

Examples of neuraminidase treatment are provided herein. In general, a proper amount of neuraminidase is added to the serum or plasma and incubated at a temperature that is suitable for the reaction (for example, at about 4, 8, 10, 15, 20, 25, 30, 35, 37, 40, 45, 50, 55, 60, 65, or 70° C.) for a suitable period of time. The amount of neuraminidase added to the reaction depends on the activity of the enzyme and the property of the serum. In some reactions, about 0.01, 0.05, 0.1, 0.2, 0.4, 0.6, 0.8, 1, 1.2, 1.4, 1.6, 1.8, 2, 2.2, 2.4, 2.6, 2.8, 3, 4, 5, 6, 7, 8, 9 or 10 units (U) neuraminidase/liter is used in the pre-treatment step. Neuraminidase may be prepared in a suitable buffer solution (e.g. 100 mM sodium acetate, pH 5.5, 0.15 M NaCl, 4 mM $CaCl_2$). In some embodiments, treatment is carried out by incubating the biological sample with neuraminidase for about or less than 10, 15, 20, 25, 30, 40, 50, 60, 90, or 120 minutes. A neuraminidase reaction may be terminated by adding a "termination solution", which is a solution that may be used to inactivate the neuraminidase enzyme, but that causes no or minimal damage to the sample. In one example, a termination solution is 1.5% sodium citrate in sodium phosphate solution, pH 8.2. In one example, a termination reaction using a termination solution is to add 5 volumes of 1.5% sodium citrate in sodium phosphate pH 8.2 to a neuraminidase reaction, and to incubate the mixture at 56° C. for 5 minutes.

In some embodiments the pre-treatment is carried out by incubating the biological sample with neuraminidase, and wherein the final concentration of the neuraminidase in the mixture is about 0.2, 0.4, 0.6, 0.8, 1, 1.2, 1.4, 1.6, 1.8, or 2 U/liter, or greater.

After the inactivation, the reaction may be cooled to room temperature. In some embodiments, the treated sample is diluted (e.g. 1:2, 1:3, 1:4, 1:5, or 1:10 dilution) prior to be used for the assays provided herein.

Assays may be conducted with serial dilutions of a biological sample, an antigen, erythrocytes, viral particles, agglutinating particles, visualization particles, antibodies, or any combination thereof. However, in some embodiments, the need for serial dilution is reduced or eliminated by the use of methods described herein for rapid agglutination assay analysis.

D. TARGET ANALYTES

The methods provided herein are used to detect a target analyte in the biological sample. The target analyte may be, without limitation, an antibody, an antigen, a viral particle, a bacterial particle, or an agglutinating particle.

D1. Antibody Target Analytes

In one aspect, methods are provided for detecting and measuring antibodies in a biological sample. In some embodiments, detectable antibodies bind selectively to a viral particle. In some embodiments, detectable antibodies bind selectively to an agglutinating particle.

In some embodiments, a sample is any antiserum that contains antibodies that bind to one or more epitopes on a viral particle having the ability to agglutinate erythrocytes, or suspected of having the ability to agglutinate erythrocytes (in the case of an antiserum being tested in the HAI). Alternatively, or additionally, the antiserum may be any antiserum that contains antibodies that bind to one or more epitopes of a hemagglutinin protein, or suspected of containing antibodies having the ability to bind to one or more epitopes of a hemagglutinin protein (in the case of an antiserum being tested in the HAI). Alternatively or additionally, the antiserum may be any antiserum that contains antibodies that bind to one or more epitopes present on an agglutinating particle. The antiserum can be serum obtained from any living source, such as a human, bird, horse, rabbit, mouse, goat, pig, guinea pig, or rat. The living source of the antiserum may have been immunized with a particular antigen, although the living source need not have been specifically exposed to the antigen. The antiserum may also be a serum produced in vitro to contain antibodies that bind to a virus, a hemagglutinin protein, or an agglutinating particle. The antibodies may be monoclonal or polyclonal. Further, the antibodies may be full length, or an antigen binding fragment, such as Fab, $F(ab)_2$, or Fv fragments and single chain antibodies. The antibodies may also be naturally occurring antibodies, humanized antibodies or chimeric antibodies. Any antibody that binds to an agglutinating virus, a hemagglutinin protein, or agglutinating particle, whatever the source, may be used in the assays. Other types of reagents that bind specifically to hemagglutinin or agglutinating particles and block or inhibit agglutination may also be used. Examples of such binders include, without limitation, aptamers and lectins.

In some embodiments, a plasma, serum, or antiserum sample is derived from a subject that has been administered with a vaccine against an agglutinating virus or agglutinating particle. Thus also provided herein are methods of determining the effective immunization of a subject, which can be assessed by detecting and/or measuring the presence of antibodies against an agglutinating virus or agglutinating particle in a sample from the subject using an HAI assay of the disclosure.

The skilled artisan will understand that the concentration of the antisera or antibodies used in a particular assay will depend on a number of different factors, such as the source of the antisera, the type of antibody in the antisera, the affinity of the antibodies in the antiserum, the concentration of non-antibody components of the antisera, the sample volume, and the source and concentration of the other components being used in an assay. Further, the concentration of the antisera to be used in an assay can be in some cases based on the known value of the lowest dilution of the antisera at which the antibodies in the antisera can block hemagglutination from occurring in a conventional HAI assay. Higher and lower concentrations of antisera may be used as starting points in an assay provided herein based on this dilution. For example, if a 1:128 dilution is the lowest dilution of the antisera at which hemagglutination can be blocked in a conventional HAI assay, dilutions of 1:64, 1:128, 1:512, 1:1024, 1:2048, 1:4096 and 1:8192 may be used. The skilled artisan will understand that any dilution of antisera may be used, or any series of dilutions, whether based on a factor of 2, or some other number. In one aspect, the concentration of the antibody in the final mixture of an assay may be about, for example, 0.1, 0.5, 1, 2, 3, 4, 5, 6, 7, 8, 9 or 10, 20, 30, 40, or 50 nM. In another aspect, the concentration of the antibody in the final mixture of an assay may be about, for example, 2 ng/mL, 5 ng/mL, 10 ng/mL, 20 ng/mL, 50 ng/mL, 100 ng/mL, 200 ng/mL, 500 ng/mL, 2 µg/mL, 4 µg/mL, 6 µg/mL, 8 µg/mL, 10 µg/mL, or 20 µg/mL. In such aspects, the dissociation constant of the antibodies in the antisera for a viral epitope ($K_D$) may be about 0.01, 0.05, 0.1, 0.5, 1, 5, 10, 20, 30, 40 or 50 nM. In one aspect, the concentration of a virus in the final assay mixture may be about 5, 10, 15, or 20 hemagglutination units/mL. Hemagglutination units (HA units) are the lowest dilution of the virus at which hemagglutination occurs in a conventional HA assay Methods of the disclosure provide improvements for detection and/or measurement of antibodies in a sample, and in some embodiments, the total amount time of carrying out the method is about or less than 500, 400, 300, 200, 180, 160, 140, 120, 100, 90, 75, 60, 45, 40, 30, 25, 50, 15, 10, or 5 minutes. In some embodiments, the total amount time of carrying out the method is between about 30 to 60 minutes.

D2. Viral Particle Analytes

In another aspect, provided herein are methods for determining the presence of a viral particle in a biological sample.

Many viruses attach to molecules present on the surface of RBCs. A consequence of this is that at certain concentrations, viral suspensions may agglutinate RBCs by binding to surface receptors or modifications of receptors, including N-acetylneuraminic acid. Multiple attachment of a plurality of RBCs to a single virus particle or bacterium results in agglutination of RBCs (hemagglutination). Viruses that promote agglutination in this way are referred to as agglutinating viruses. In some embodiments, methods of the disclosure are used to detect or measure agglutinating virus(es). In other embodiments, methods of the disclosure are used to detect or measure antibodies to agglutinating virus(es).

Agglutinating viruses include viruses of many different types, including, but not limited to, picornavirus, coronavirus, togavirus, flavirvirus, rhabdovirus, paramyxovirus, orthomyxovirus, bunyavirus, arenavirus, reovirus, retrovirus, papilomavirus, parvovirus, herpesvirus, poxvirus, hepadnavirus, and spongiform virus. Other viruses include influenza, herpes simplex virus 1 and 2, measles, dengue, smallpox, polio, HIV, H1N1 Solomon Islands, H3N2 Wisconsin virus, avian H5N1 Vietnam virus, hepatitis B virus (HBV), hepatitis C virus (HCV), and any strain of influenza virus.

Further agglutinating viruses include viruses of nonhuman primates, non-limiting examples of which are Aotine herpesvirus 1, Aotine herpesvirus 3, Cercopithecine herpesvirus 1 (B virus, HV simian), Cercopithecine herpesvirus 2 (SA8), Cercopithecine herpesvirus 3 (SA6), Cercopithecine herpesvirus 4 (SA15), Cercopithecine herpesvirus 5 (African green monkey cytomegalovirus), Cercopithecine herpesvirus 6 (Liverpool vervet monkey virus), Cercopithecine herpesvirus 7 (Patas monkey HV; MMV or PHV delta HV), Cercopithecine herpesvirus 8 (Rhesus monkey cytomegalovirus), Cercopithecine herpesvirus 9 (Medical Lake macaque LV simian varicella HV), Cercopithecine herpesvirus 10 (Rhesus leukocyte assoc. LV strain IT), Cercopithecine herpesvirus 12 (LV-papio, baboon HV), Cercopithecine herpesvirus 13 (Herpesvirus cyclopis), Cercopithecine herpesvirus 14 (African green monkey EBVlike virus), Cercopithecine herpesvirus 15 (Rhesus EBV-like HV), Ateline herpesvirus 1 (Spider monkey HV), Ateline herpesvirus 2 (HV ateles), Callitrichine herpesvirus (HV saguinus), Callitrichine herpesvirus (SSG, marmoset cytomegalovirus), Cebine herpesvirus 1 (Capuchin HV), Cebine herpesvirus 2 (Capuchin HV), Pongine herpesvirus 1 (Chimpanzee HV; pan HV), Pongine herpesvirus 2 (Orangutan HV), Pongine herpesvirus 3 (Gorilla HV), Saimiriine herpesvirus 1 (Marmoset HV, herpes T, HV), tamarinus, HV platyrrhinae, (type Saimiriine herpesvirus 2) Squirrel monkey HV, and HV saimiri.

Agglutinating viruses may also refer to viruses of mammals including, but not limited to: Bovine herpesvirus 1-5, Ovine herpesvirus 1-2, Alcelaphine herpesvirus 1, Parvovirus (including mice minute virus, Aleutian mink disease, bovine parvovirus, canine parvovirus, chicken parvovirus, feline panleukopenia, feline parvovirus, goose parvovirus, HB parvovirus, H-1 parvovirus, Kilham rat lapine parvovirus, mink enteritis) Erythrovirus (including adeno-associated type 1-5, bovine adeno-associated, canine adeno-associated, equine adeno-associated, ovine adeno-associated).

Further non-limiting examples of agglutinating viruses may include: Cauliflower mosaic, Badnaviruses, Geminiviruses, Plant Retroviruses, Cryptoviruses, Rhabdoviridae, Tomato Spotted mosaic, Tenuiviruses, Potato Virus, Potyviridae, Closteroviruses, Turnip Yellow mosaic, Tomato Bushy mosaic, Luteoviruses, Sequiviridae, Tobacco mosaic, Cowpea mosiac, Pean Enation mosaic, Red Clover vein mosaic, Brome mosaic, Cucumber mosaic, Alfalfa mosaic, Barley yellow mosaic, Beet Necrotic yellow vein, and dsRNA viruses.

Viruses from the following families are also included for use in methods of the disclosure: Baculoviridae and Nudiviruses, Polydnaviridae, Ascoviridae, Nodaviridae Tetraviridae, Tetraviridae, Tombusviridae, Coronaviridae, Flaviviridae, Togaviridae, Bromoviridae, Barnaviridae, Totiviridae, Partitiviridae, Hypoviridae, Paramyxoviridae, Rhabdoviridae, Filoviridae, Orthomyxoviridae, Bunyavinrdae, Arenaviridae, Leviviridae, Picornaviridae, Sequiviridae, Comoviridae, Potyviridae, Calciviridae, Astroviridae, Nodaviridae, Inoviridae, Microviridae, Geminiviridae, Circoviridae, Parvoviridae, Haepadnaviridae, Retroviridae, Cystoviridae, Reoviridae, Birnaviridae, Myoviridae, Siphoviridae, Podoviridae, Tectiviridae, Corticoviridae, Plasmaviridae, Lipothrixviridae, Fuselloviridae, Poxviridae, African swine fever-like viruses, Iridoviridae, Phycodnaviridae, Baculoviridae, Herpesviridae, Adenoviridae, Papovaviridae, Polydnaviridae, Picornaviridae, Caliciviridae, Astroviridae, Togaviridae, Flaviviridae, Coronaviridae, Arterivirus, Paramyxoviridae, Rhabdoviridae, Filoviridae, Orthomyxoviridae, Bunyaviridae, Arenaviridae, Reoviridae, Birnaviridae, Retroviridae, Hepadnaviridae, Circoviridae, Parvoviridae, Papovaviridae, Adenoviridae, Herpesviridae, Poxviridae, and Iridoviridae.

The skilled artisan will understand that the concentration of virus used in a particular assay will depend on a number of different factors, such as the identity of the virus, sample volume, and the source and concentration of the other components being used in an assay. Further, the concentration of the virus to be used in an assay will generally be based on the known value of the lowest dilution of the virus at which hemagglutination occurs in a conventional HA assay. This dilution is considered to be 1 hemagglutination unit ("HA unit" or "HAU"). Higher and lower concentrations of virus, based on 1 HAU, may be used as starting points in an assay. For example, if a 1:128 dilution is the lowest dilution of the virus at which hemagglutination occurs in a conventional HA assay, dilutions of 1:64, 1:128, 1:256, 1:512, 1:1024, 1:2048, 1:4096 and 1:8192 may be used. The skilled artisan will understand that any dilution of virus may be used, or any series of dilutions, whether based on a factor of 2, or some other number.

D3. Bacterial Analytes

In some embodiments, methods of the disclosure can be used to detect bacteria, which may have the ability to bind cell-surface molecules in RBCs or visualization particles and induce aggregation/agglutination.

D4. Agglutinating Particle Analytes

In one some embodiments, methods of the disclosure can be used to detect any particle that can bind to and cause aggregation of cells or microspheres. Such particles are referred to herein as "agglutinating particles". Agglutinating particles include, without limitation, viruses, bacteria, viral particles, allergens, and antibodies. In other examples, agglutinating particles include proteins and carbohydrates that have binding specificity the surface of RBCs or other cells (e.g. lectins). Furthermore, in the context of microspheres (which, as discussed below, may be prepared to have a wide variety of molecules on their surface), any molecule that may bind to a molecule on the surface of a microsphere can function as an agglutinating particle.

E. ERYTHROCYTES

In one aspect, the disclosure provides methods for detecting and measuring agglutination of red blood cells ("RBCs"), a term used interchangeably with "erythrocytes."

Erythrocytes are oxygen-delivering cells that contain hemoglobin, an iron-containing biomolecule that can bind oxygen and is responsible for the blood's red color. Erythrocytes from various organisms may be used in the methods disclosed herein, as long as the cells have the potential to agglutinate in the presence of an agglutinating particle such as a virus. Suitable erythrocytes include, without limitation, avian erythrocytes, such as goose, chicken, duck, and turkey red blood cells, and mammalian erythrocytes, such as human erythrocytes, guinea pig erythrocytes, mouse erythrocytes, rat erythrocytes, bovine erythrocytes, equine erythrocytes, goat erythrocytes and sheep erythrocytes. Human erythrocytes may be from a donor of any blood group, such as group A erythrocytes, group B erythrocytes, group AB erythrocytes, and group O erythrocytes.

In some embodiments, erythrocytes may be assayed for agglutination, and the concentration of the erythrocytes can be selected such that they are present at a concentration of below about 0.01% hematocrit, below about 0.05% hematocrit, below about 0.1% hematocrit, below about 0.15% hematocrit, or below about 0.2% hematocrit.

The hematocrit (Ht or HCT) or packed cell volume (PCV) or erythrocyte volume fraction (EVF) is the percentage of blood volume that is occupied by red blood cells.

E1. Fixation of Erythrocytes

In some embodiments, erythrocytes that are assayed using the methods provided herein are pre-treated.

The red blood cell reagent used in the traditional hemagglutination methods must be freshly prepared using an elaborate wash procedure. The traditional procedure is labor intensive, inconvenient, and time consuming. In contrast, in some embodiments, methods provided herein use single stable fixed red cell preparation, so no reagent preparation is required.

Pre-treatment can include pre-fixation of erythrocytes to produce pre-fixed erythrocytes. Pre-fixation of erythrocytes provides numerous advantages, including reduction of assay time due to elimination of the need to freshly prepare erythrocytes from blood samples, and reproducibility of agglutination assays due to use of uniform pre-fixed erythrocyte samples. Methods of fixing erythrocytes are known in the art and include those described in U.S. Pat. No. 5,994,139.

In some embodiments, erythrocytes are pre-fixed by treatment with an organic aldehyde including monoaldehydes such as formaldehyde, aldehydes such as glutaraldehyde, and polymeric forms such as paraformaldehyde which are in equilibrium with formaldehyde. In some embodiments, erythrocytes are pre-fixed by treatment with glutaraldehyde. The fixed cells are essentially indefinitely stable (in contrast to fresh red cells which have to be prepared daily and will vary from day to day). Fixation does not inactivate the cell surface receptors to which the viral hemagglutinin binds.

In some embodiments, animal red blood cells are produced from freshly washed animal RBCs by brief exposure to a glutaraldehye-buffer solution and exhaustive washing in saline. This treatment largely preserves the native antigenicity of the erythrocytes while rendering the cells generally resistant to lysis by osmotic shock, freeze-thawing or immune hemolysis. These reagents may be used directly in hemagglutination procedures, or may be coupled with various proteins for hemagglutination testing. The glutaraldehyde stabilized RBCs are generally stored as cell suspension in saline with 0.1% sodium azide.

Red blood cells stabilized by glutaraldehyde fixation are available from commercial sources, such as Fitzgerald Industries (Acton, Mass.), which provide glutaraldehyde stabilized animal red blood cells from bovine, cat, chicken, dog, goat, guinea pig, hamster, horse, monkey, mouse, pig, rat, sheep, turkey, and rabbit, all of which can be used in the methods provided herein.

In some embodiments, the erythrocytes are turkey red cell stabilized by glutaraldehyde fixation. In some embodiments, fresh red cells and cells from different animal species can also be used.

F. OTHER TYPE OF CELLS

In some embodiments, cells other than red blood cells can be used for the methods provided herein, as long as these cell agglutinate in the presence of a viral particle, antibody, or other agglutinating particle.

G. MICROSPHERES

In some embodiments, methods of the disclosure are used to measure aggregation of any non-cell molecule or particle, provided the aggregates are large enough to be detected microscopically. Such particles are referred to herein as "microspheres". Thus, in the assays provided herein, RBCs can be replaced with microspheres, the surface of which are coupled with an antigen or antibody that binds selectively to the viral particle, antibody, or other agglutinating particle or substance to be detected.

Examples of suitable microspheres include latex microspheres and other microspheres that can be readily bound to viral particles, antibodies, proteins, carbohydrates, or antigens and agglutinated. In one embodiment, the microspheres are beads. In some embodiments, microspheres contain latex, gold, glass, or silica. In one embodiment, the microspheres are latex microspheres coated with a receptor that binds to a viral particle. In an embodiment, microspheres are coated with hemagglutinin protein, or a blood group antigen (e.g. antigen A, B, D, etc.).

In some embodiments, methods of the disclosure employ antigen-coated microspheres for agglutination tests. The name notwithstanding, microspheres may be of any shape, including, without limitation, spherical, cuboid, cylindrical, and irregular. They may comprise any material suitable for attaching antigen and use in agglutination assays.

Antigen can be coupled to a microsphere. The methods of attachment of antigens to microsphere beads are known in the art. Coupling may be to the surface of the microsphere or to an internal surface that is accessible from the outside surface. Antigens can be coupled to beads such as those provided by Luminex Corporation (Austin, Tex.) by a two-step carbodiimide process according to the manufacturer's recommendations. In some embodiments, the antigen may be adsorbed or covalently attached to the microsphere.

In some embodiments, a plurality of antigens can be used, each coupled to separate or the same microspheres. Antigens used for coupling to microspheres include antigenic portions of viruses that can be recognized by antibodies or agglutinating particles using methods provided herein. Antigenic portions of viruses include, but are not limited to, viral membrane proteins and nonstructural proteins. In some embodiments, a mixture of microspheres, each coupled to a different antigen or antibody can be used.

H. NONSPECIFIC PROTEINS AND OTHER MOLECULES

In some embodiments, a nonspecific protein is added to an agglutination assay to accelerate the agglutination reaction. Addition of a nonspecific protein can accelerate the reaction by about 2-fold, 3-fold, 4-fold, 5-fold, 6-fold, 7-fold, 8-fold, 10-fold, 20-fold, or by more than 30-fold. Suitable nonspecific proteins include albumins including, but not limited to, albumins from various animals, such as bovine, horse, sheep, goat, chicken and human. Other non-limiting examples of albumins include bovine serum albumin, human serum albumin, chicken egg albumin, bovine lactalbumin and human lactalbumin.

In addition, other macromolecular species may also be used to accelerate the agglutination, such as synthetic polymers (e.g. polyethylene glycol (PEG), polyethyleneoixde (PEO)), sugar polymers (e.g. dextran), dextran sulfate, diethylaminoethyl-dextran (DEAE-dextran) and polyvinyl pyolidone.

The amount of nonspecific additive to be added to the assay can vary, and generally is about any amount between 0.1-50 mg/ml. In certain methods, 0.5, 1, 2, 3, 4, 5, 6, 7, 8, 9, 10, 15, 20, 25, 30, 35, 40, 45, or 50 mg/ml of nonspecific additive is added to the assay.

The nonspecific additive can be added to the diluent buffer or other buffer/reagent used in the assays.

I. EXEMPLARY ADVANTAGES OF PROVIDED AGGLUTINATION ASSAYS

The compositions, methods, systems, and devices described herein provide multiple different advantages for agglutination assays over conventional agglutination assays.
I1. Increased Sensitivity In one aspect, provided herein are methods to increase the sensitivity for detecting agglutination over conventional agglutination assays.
I1a. Increased Sensitivity—Image Analysis In one embodiment, agglutination assay sensitivity may be increased by the use of image analysis to analyze agglutination reactions (discussed further below). The use of image analysis may increase assay sensitivity over conventional agglutination assays by about 2, 3, 4, 5, 6, 7, 8, 9, 10, 15, 20, 25, 30, 40, 50, 75, or 100-fold.
I1b. Increased Sensitivity—Concentration/Dilution Steps In another embodiment, agglutination assay sensitivity may be increased by concentrating a reaction mixture containing agglutinating particles (e.g. viral particles) and visualization particle (e.g. RBCs or microspheres), followed by dilution of the concentrated material and subsequent analysis of agglutination. In this method, the agglutinating particles and visualization particles are brought into close proximity in the concentration step to facilitate binding of the agglutinating particles to the visualization particles. Then, in the step of diluting the concentrated material, only specifically aggregated visualization particles remain agglutinated (i.e. visualization particles that are non-specifically aggregated during the concentration step do not remain aggregated during the dilution step). Using this method, less agglutinating particle may be used in the assay to produce detectable agglutination. Correspondingly, in HAI assays, less antibody in the sample will be needed to cause agglutination inhibition. Thus, since less agglutinating particle and/or less antibody is needed to cause agglutination or agglutination inhibition, this method may increase the sensitivity of agglutination assays.

In one embodiment, agglutination assay sensitivity may be increased by performing an agglutination assay with a method including the following steps. First, a biological sample suspected of containing an antibody of interest is mixed with an agglutinating particle and visualization particles and incubated. In some aspects, the biological sample may be incubated with the agglutinating particle before the addition of the visualization particles. Second, the reaction containing of the agglutinating particles, visualization particles, and sample suspected of containing an antibody of interest is centrifuged to generate a pellet. Typically, centrifugation with this method is gentle (hundreds to low thousands×g for a few minutes) so as not to generate complexes that would be difficult to resuspend. Third, the supernatant is removed, and the pellet is washed one or two times with a buffer that would not interfere with the agglutinated particles or visualization particles. Fourth, the washed pellet is resuspended in buffer. Fifth, the resuspended reaction mixture is analyzed for agglutination.

In another embodiment, in an agglutination assay using antibodies as the agglutinating particles, sensitivity of the assay may be further increased by adding to a washed agglutination reaction an antibody against the type of antibody of interest. In one embodiment, in an agglutination reaction containing the concentration/dilution steps described above, if the antibody of interest is human, when the washed pellet is resuspended, anti-human globulin is also added to the resuspended pellet. After incubation of the resuspended pellet with the anti-human globulin, the resuspended reaction is analyzed for agglutination. In this method, the anti-human globulin binds to the antibody of interest, which may be bound to the visualization particle. Since the anti-human globulin may bring together multiple antibodies of the antibodies of interest, and each of these antibodies may be bound to one or more visualization particles, the addition of the anti-human globulin may increase the agglutination assay sensitivity. The specificity of this method may be further increased by using anti-human IgM, IgG, or IgA, rather than anti-human globulin, in order to identify particular antibody types.
I2. Increased Speed In one aspect, the assays provided herein may provide advantages in terms of speed. Traditional assays call for a pre-treatment step with incubation of at least 12-18 hours. In some methods of the disclosure, the pre-treatment step is performed in less than 15 minutes, less than half an hour, less than one hour, or less than two hours. Furthermore, methods of the disclosure eliminate the need for fresh preparation of erythrocytes, a process that can take 4 hours using traditional procedures. In traditional methods, incubation with viral antigen and erythrocytes are performed as two separate steps, but in some embodiments disclosed herein, viral antigen and erythrocytes are added together in a single step. Thus, in some embodiments, the HA assay or HAI assay of the disclosure is carried out in less than one hour, less than 1.5 hours, less than 2 hours, less than 2.5 hours, or less than 3 hours.

Methods of the disclosure provide improvements for detection and/or measurement of viruses in a sample, and in some embodiments, the total amount time of carrying out the method is less than 500, 400, 300, 200, 180, 160, 140, 120, 100, 90, 75, 60, 45, 30, 15, 10, or less than 5 minutes. In some embodiments, the total amount time of carrying out the method is between 30 to 60 minutes.
I2a. Increased Speed—Image Analysis In one embodiment, agglutination assay speed may be increased by the use of image analysis to analyze agglutination reactions (discussed further below).
I2b. Increased Speed—Reagents and Assay Steps In other embodiments, agglutination assay speed may be increased by the use of improved reagents and/or assay steps to accelerate the performance and/or analysis of agglutination reactions. For example, as described elsewhere herein, improvements in any one or more of sample pre-treatment (e.g. by the use of neuraminidase), use of pre-fixed RBCs or microspheres, use of combined assay steps (e.g. by the mixing of agglutinating particle, visualization particle, and antibody-containing sample in a single incubation, rather than first incubating the agglutinating particle and antibody-containing sample before addition of the visualization particle), and improvement in assay medium composition may reduce the time necessary to obtain accurate agglutination assay results.

13. Decreased Volume

In one aspect, methods provided herein may provide advantages in terms of reaction volume. In some embodiments, agglutination assay methods provided herein may be performed in a reaction volume of about 50, 40, 30, 20, 10, 9, 8, 7, 6, 5, 4, 3, 2, 1 microliters, or less. In some embodiments, agglutination assays provided herein may be performed using about 50, 40, 30, 20, 10, 9, 8, 7, 6, 5, 4, 3, 2, 1, 0.8, 0.6, 0.4, 0.2, 0.1 microliters, or less of blood sample.

J. GENERAL—AGGLUTINATION ASSAYS

Detection of agglutination generally involves taking images of the agglutination reaction product using an imaging device, such as a scanner, a camera, detector, or sensor. In some embodiments, an imaging device is coupled to a microscope.

In general, the assay is carried using a device that is capable of holding the reactions, such as a 96-well microtiter plate, or its equivalent. A pre-treated biological sample containing the antibody to be detected is optionally serially diluted in the plate with a diluent buffer (e.g. PBS with BSA). Next, viral particles may be added to each well and the content of the each well is gently mixed. Then, pre-fixed RBCs suspension may be added, followed by gently mixing. The reaction is incubated for a suitable period of time, for example, a total of about 15 minutes. However, a total incubation shorter or longer than 15 minutes may also be used, such as about 5, 10, 20, 25, 30, 35, 40, 50, 60 minutes, or shorter or longer. The incubation may be carried at room temperature (i.e., 25° C.), or at a temperature that is lower or higher than room temperature, such as about 4, 8, 12, 14, 16, 20, 30, 35, 40, 45, 50, 55, 60, 65, or 70° C. The temperature and duration of incubation can be optimized to achieve both speed and accuracy of the assays. The plate is then read on a scanner and a final endpoint image is taken of the plate, preferably when the plate is tilted at 20-75°, such as at about 20, 25, 30, 35, 40, 45, 50, 55, 60, 65, 70, or 75° relative to horizontal.

In some embodiments, the image of the agglutination is captured with an optical device containing a microscope. In these embodiments, the assay is generally carried as described above, except after the pre-fixed RBCs or visualization particles are added to the reaction, a small sample (e.g. 1-2 μL) from the wells is transferred directly into a cuvette, and imaged under an optical device containing a microscope. Images are collected and analyzed to calculate association factors as described in more detail herein.

The duration for performing the agglutination assay is generally optimized to achieve both speed and accuracy of the assay. In some embodiments, performing the assay and detecting agglutination takes place in less than one hour, such as about 10, 15, 20, 30, 40, 50, or 60 minutes. In some embodiments, performing the assay and detecting agglutination takes place in more than one hour, but less than 2, 3, 4, 5, 6, 7, or 8 hours.

In some embodiments, the agglutination assay may be performed on a system or device wherein one or more steps of the agglutination assay are automated and/or controlled via a cloud computing infrastructure. For example, agglutination assays as described herein may be performed on a system or device as described in U.S. application Ser. No. 13/244,947 or U.S. application Ser. No. 13/355,458, which are hereby incorporated by reference in their entirety.

In one embodiment, a device includes a component capable of adding an agglutinating particle to a sample under a condition suitable for agglutination, thereby initiating an agglutination assay; a component capable of obtaining a set of images of the agglutination assay; and a component capable of analyzing the set of images to measure the agglutination of the sample. The component capable of analyzing a set of images to measure the agglutination of the sample may be part of the same apparatus within the device as the component that is configured to obtain more than one image of the agglutination assay. The component capable of analyzing a set of images to measure the agglutination of the sample may be embedded within the device. The component capable of analyzing a set of images to measure the agglutination of the sample may be configured to perform multiple types of analysis and/or it may be used for multiple applications within the device. A component capable of analyzing a set of images to measure agglutination of the sample may be located remotely from the device. A component capable of analyzing a set of images to measure the agglutination of the sample may be located in a cloud computing infrastructure (e.g. cloud computing). A component capable of analyzing a set of images to measure the agglutination of the sample may be located in the cloud, and the device may be configured to be dynamically controlled from the cloud. In some embodiments, the device is configured to affect a secondary procedure based on the results of an agglutination assay analysis. In some embodiments, a device capable of performing an agglutination assay as described herein may be configured as a device described in, for example, U.S. Ser. No. 13/244,947, which is herein incorporated by reference in its entirety.

In one embodiment, a system disclosed herein may include a device capable of adding an agglutinating particle to a sample under a condition suitable for agglutination, thereby initiating an agglutination assay; a camera capable of obtaining a set of images of an agglutination assay; and a computer capable of analyzing the set of images to measure the agglutination of the sample. The computer configured to analyze a set of images to measure the agglutination of the sample may be part of the same apparatus within the system as the camera that is configured to obtain a set of more than one image of the agglutination assay. The computer configured to analyze a set of images to measure agglutination of the sample may be embedded within the system. The computer configured to analyze a set of images to measure the agglutination of the sample may be configured to perform multiple types of analysis and/or it can be used for multiple applications within the system. The computer configured to analyze a set of images to measure the agglutination of the sample may be located remotely from a camera configured to obtain a set of more than one image of the agglutination assay. The computer configured to analyze a set of images of an agglutination assay may be located in the cloud. The computer configured to analyze a set of images of an agglutination assay may be located in the cloud, and the system may be configured to be dynamically controlled from the cloud. The system may be configured to affect a secondary procedure based on the results of an agglutination assay analysis. In some embodiments, a system capable of performing an agglutination assay as described herein may be configured as a system described in, for example, U.S. Ser. No. 13/244,947, which is herein incorporated by reference in its entirety.

III. Detection and Image Analysis

In one aspect, the present disclosure provides for advantageous objective methods of analyzing aggregation, agglutination, or hemagglutination based on image analysis.

In a traditional agglutination assay in a conical tube or well (as in a titer plate), agglutination is determined by visual observation of either the reduced mobility of RBCs at the bottom of a well (in the case of agglutination), or by the limited flow of packed RBCs under gravity when the titer plate is tilted (in the case of lack of agglutination). The reduced mobility of RBCs in the case of agglutination is due to attractive forces between RBCs and an agglutinating particle.

To read agglutination reactions, several optical (visual) methods have been used. However, these existing methods detect binding of RBCs to each other by observing a bulk material property of the suspension by simple visual inspection.

In one aspect, provided herein are methods of analyzing agglutination based on image analysis. In one embodiment, image analysis methods are used to analyze the bulk movement of RBCs or visualization particles in an agglutination assay in a conical well or tube. In another embodiment, image analysis methods are used to analyze microscopic images of RBCs or visualization particles in suspension in an agglutination assay, in order to interrogate the fine structure of the RBC or visualization particle suspension.

A. Image Analysis of Bulk Movement of RBCs/Visualization Particles

In one aspect, provided herein are methods for image analysis of bulk movement of RBCs and visualization particles. As described above and in FIG. 3, in a conical (V-shaped) reaction vessel (e.g. tube or reaction well), unagglutinated cells generally settle in a loosely packed "button" at the bottom of the vessel, whereas agglutinated cells generally adhere more tightly to other cells. Accordingly, if a conical reaction vessel containing agglutinated cells is tilted, the cells will generally not leave the bottom of the vessel, as the cells are relatively tightly adhered to each other. In contrast, if a reaction vessel containing unagglutinated cells is tilted, some cells will generally move away from the bottom of the well under gravity, leading to the formation of a cell pellet in a "teardrop" shape. Multiple methods for image analysis of agglutination assays related to the above events are provided herein.

A1. Bulk Movement—Image Analysis at Designated Locations in Reaction Vessels

Figure 6A:
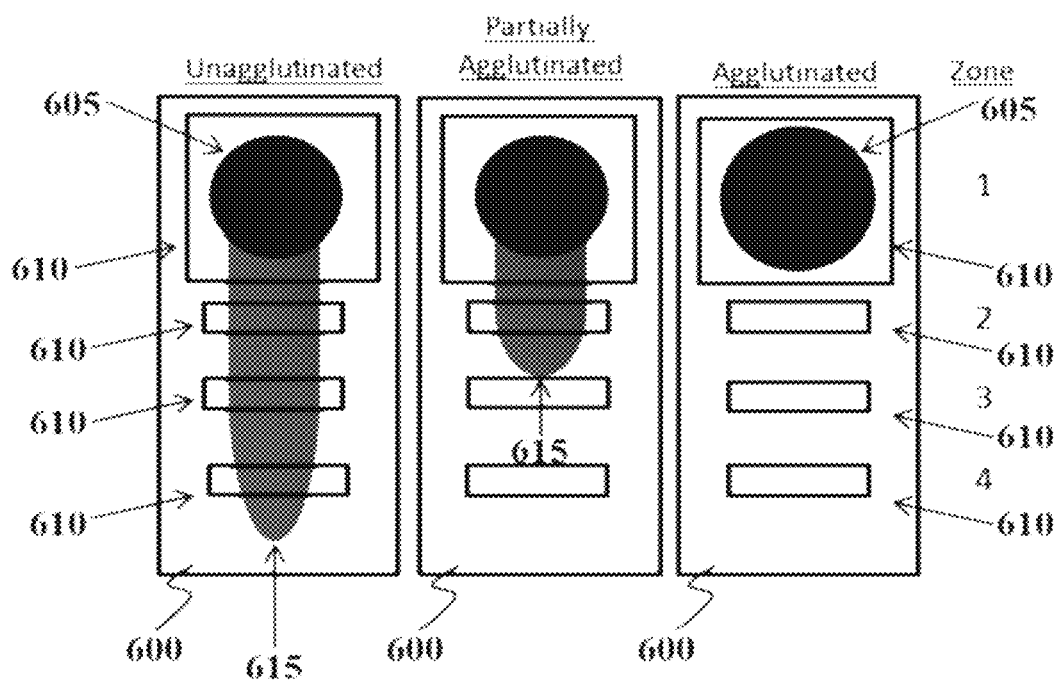
FIG. 6A depicts movement of visualization particles across zones in unagglutinated, partly agglutinated, and agglutinated samples.
Figure 6B:
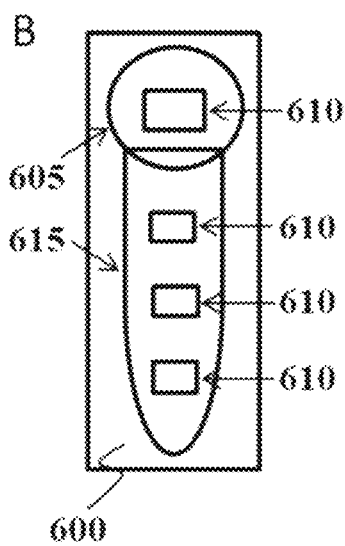
FIG. 6B depicts zones that are smaller than the area of visualization particles.

In one embodiment, a method is provided for image analysis of agglutination reactions using designated locations in a reaction vessel (e.g. reaction tube or well). FIG. 6 shows schematic diagrams relating to the method. In this method, zones 610 are included in and/or next to the bottom of a reaction vessel 600. The bottom of the reaction vessel 600 may contain a pellet of cells 605. Images of the reaction vessel may be taken before, during, and/or after tilting of the reaction vessel. The position of the cells may be determined with reference to the designated zones in the reaction vessel, which may be used to determine the level of agglutination of the sample and/or to perform related calculations. In some situations, a "teardrop" of cells 615 may form upon tilting of the reaction vessel. Cells that are not agglutinated may form a teardrop shape, whereas cells that are agglutinated may not form a teardrop shape. Cells that are agglutinated may remain in a pelleted or "button" shape. In some situations, an assay may result in partial agglutination of the cells. The zones 610 may have outlines which encompass the regions containing button cells and/or teardrop cells and some of the background (FIG. 6A), or the zones may have smaller outlines that only occupy regions that may contain button or teardrop cells (FIG. 6B).

In an embodiment, image analysis of agglutination reactions using designated zones in a reaction vessel may include one or more of the following steps:

First, a digital image of a well containing a reaction mixture is taken.

Second, the image is oriented using pattern recognition techniques either by reference to fiducial marks on the assay wells or by recognition of the button or teardrop.

Third, the image is oriented relative to zones in the reaction vessel. Optical signal is measured pixel by pixel over each zone. The measured signal may be, for example, using white light illumination: a) % transmitted light (T) (grey scale when the image is obtained by back lighting), or b) % reflected light (R) (grey scale when the image is front lighting). Percent transmitted light may be determined by taking a ratio of light transmission when cells are present to that when no cells are present in the light path; percent reflectance may be determined in an analogous fashion. Each of the % T and % R measurements involves an illumination source and a detector. In the case of transmittance, the sample may be placed in an optically clear vessel in line and in between the illumination source and detector. If the light coming out of the illumination source has an intensity Io, and the light reaching the detector (after passing through the sample) has an intensity I, the transmittance may be calculated using T=I/Io.

Fourth, transmission (% T) or reflectance (% R) may be converted to absorbance (A), according to the formula: (A=–LOG [% T]) (Beer's law) or K/S (where K=Absorbance and S is scattering) respectively. Beer's law is the relation between measured absorbance and analyte concentration.

A and K/S are directly related to the concentration of light absorbing species as follows: A=concentration*$\epsilon$M*l*C (where $\epsilon$M is the molar extinction coefficient, l is path length of the sample, and C is the concentration of the of the analyte of interest, which is the absorbing species); K/S= $(1-(0.01R)^2)/(2*0.01R)$ respectively. For scattering, the illumination source is at approximately a 90-degree angle relative to the detector. The scattering intensity is the intensity of light (from the illumination source) scattered by the sample (collected by the detector).

Figure 7:
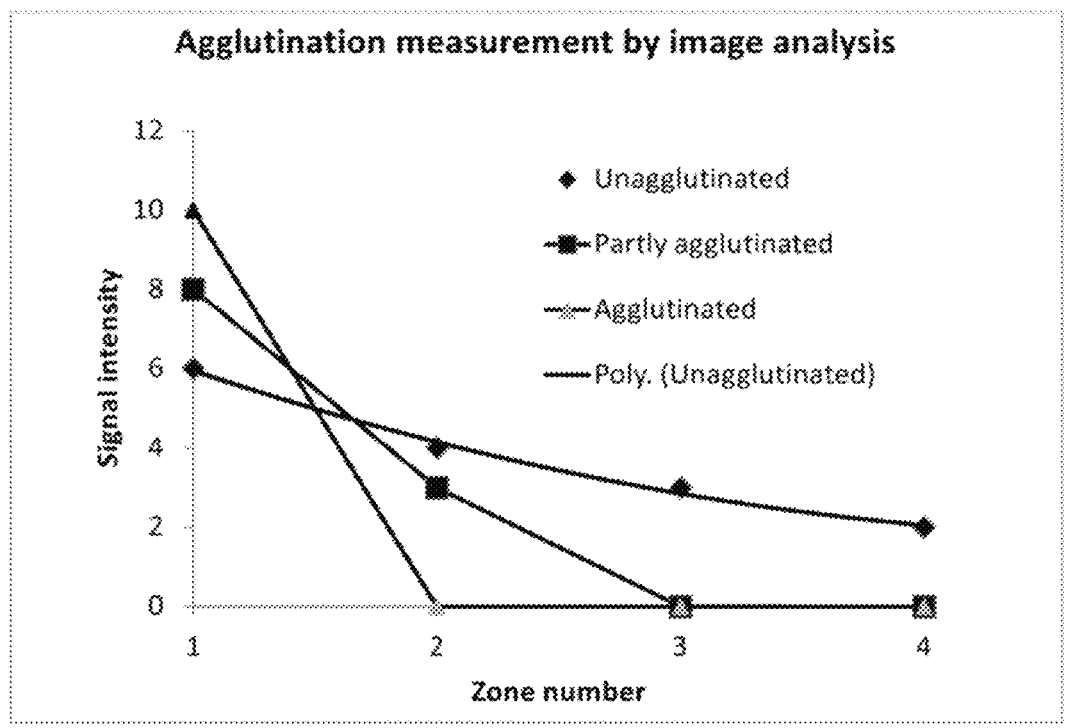
FIG. 7 shows a sample graph of signal intensity vs. zone number for the samples depicted in FIG. 6

As shown in FIG. 7, when signal intensity (% T or % R) is plotted against zone number, a relationship indicating response versus extent of aggregation (arbitrary scale) is obtained.

While the equations above apply to a single wavelength, if white light is used, the A or K/S values will represent averages over a range of wavelengths. These still provide acceptable results for agglutination analysis.

In some embodiments, using Absorbance or K/S as the measured signal, signal greater than background may be averaged within each zone. Also, if Absorbance or K/S is greater than an arbitrary threshold, the signal may be set to one or zero if it is less than the cut-off for analysis.

A2. Bulk Movement—Image Analysis Using Scanning

Figure 8:
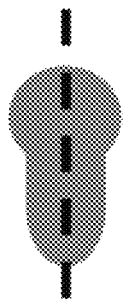
FIG. 8 depicts an axis through a button and teardrop, as may be used for analysis of bulk movement of visualization particles by image analysis using scanning
Figure 9:
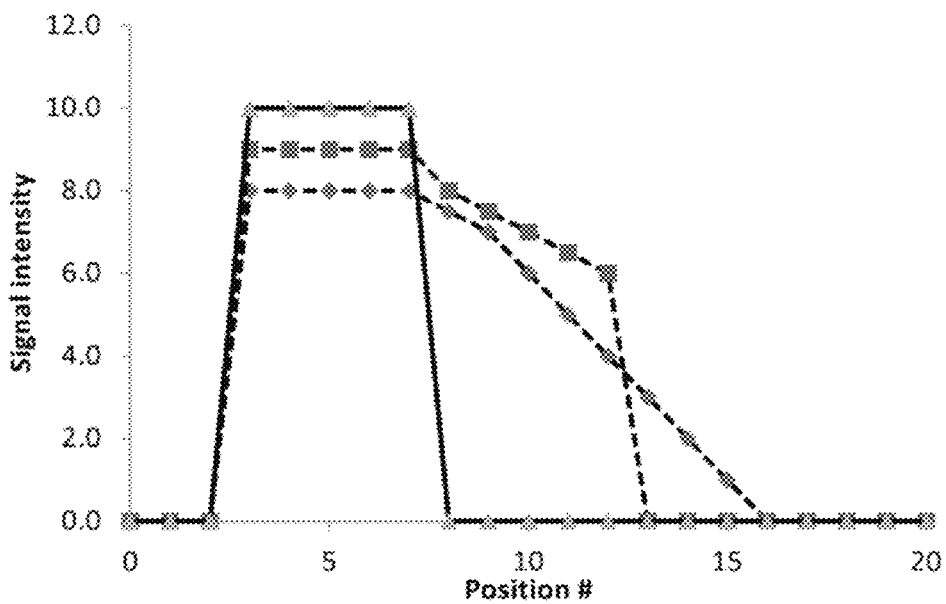
FIG. 9 shows a sample graph of signal intensity vs. position number along an axis as depicted in FIG. 8 for unagglutinated, agglutinated, and partially agglutinated samples. The line marked by triangles is agglutinated sample, the line marked by squares is partly agglutinated sample, and the line marked by diamonds is unagglutinated samples.

In one embodiment, a method is provided for image analysis of agglutination reactions using scanning of the packed cells. The packed cells may include a button and/or teardrop region. FIG. 8 shows a schematic diagram relating to the method. In this method, an agglutination reaction is performed in a conical vessel, and the reaction vessel is then tilted. Next, a scan zone along the long axis of the button and/or or teardrop may be established. The axis for analysis may be longer than the combined length of the button and/or teardrop. Positions along the axis may be assigned, such as Position 0 being the start of the axis, being outside of the button, and Position 20 being the end of the axis, being outside the teardrop. The number of positions may be selected arbitrarily, based on the best combination of speed and accuracy. The length of the axis may be interrogated for an optical signal, such as % T or % R. The signals may be plotted against positions along the axis. FIG. 9 shows a representative graph of optical signal intensity vs. position for multiple types of samples (agglutinated, partially agglutinated, and unagglutinated), along an axis as shown in FIG. 8. The optical signals along the length of the button and/or teardrop may be used to determine the level of agglutination in the sample and/or to perform related calculations.

In one embodiment, image analysis of agglutination reactions using scanning of the button and/or teardrop may include one or more of the following steps:

First, a digital image of a well containing a reaction mixture is taken.

Second, the image is oriented using pattern recognition techniques either by reference to fiducial marks on the assay wells or by recognition of the button or teardrop.

Third, a scan zone along the long axis of the teardrop and/or button is interrogated for % T or % R.

Fourth, optical signal (as defined above under "Bulk Movement—Image Analysis at Designated Locations in Reaction Vessels") is measured pixel-by-pixel along the axis.

Fifth, signal greater than background may be averaged over several pixels down and at right angles to the axis.

Sixth, signal is plotted against positions along the axis.

A3. Bulk Movement—Image Analysis of Area or Perimeter

Figure 10:
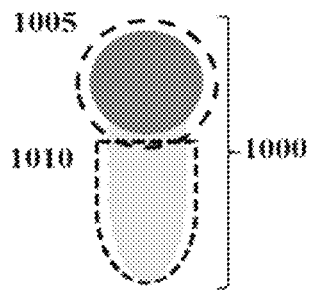
FIG. 10 depicts a schematic showing identification of the perimeter of the button (1005/Area A) and teardrop (1010/Area B) area of packed visualization particles, as may be used for analysis of bulk movement of visualization particles by image analysis of areas or perimeter.

In one embodiment, a method is provided for image analysis of agglutination reactions using determination of the area and/or perimeter of the packed cells of an agglutination reaction. Packed cells may include a button and/or teardrop region. In some embodiments, the area and/or perimeter of the button and/or teardrop regions of packed cells may be determined FIG. 10 shows a schematic diagram relating to the method. In this method, an agglutination reaction is performed in a conical vessel, and the reaction vessel is then tilted. Next, an image may be obtained of the entire tilted sample 1000. Optical signal may then be measured over the image. Then, pattern recognition methods may be used to identify the button and/or the teardrop region (if any) of a sample. In FIG. 10, the sample has a button area 1005 (area A) and a teardrop area 1010 (area B). The area and/or perimeter of the button and/or teardrop may then be measured. This information may be used to determine the level of agglutination in the sample and/or to perform related calculations.

In one embodiment, image analysis of agglutination reactions using analysis of the area and/or perimeter of the button and/or teardrop may include one or more of the following steps:

First, a digital image of a well containing a reaction mixture is taken.

Second, the image is oriented using pattern recognition techniques either by reference to fiducial marks on the assay wells or by recognition of the button or teardrop.

Third, the image is oriented relative to zones as described above under "Bulk Movement—Image Analysis at Designated Locations in Reaction Vessels"

Fourth, optical signal (as defined above under "Bulk Movement—Image Analysis at Designated Locations in Reaction Vessels") is measured pixel-by-pixel over the entire image.

Fifth, pattern recognition methods are used to identify areas which correspond to the button, and, when present, the teardrop. These areas will have significantly greater absorbance than the background. The area and/or perimeter of the button and/or teardrop are measured. In some embodiments, for each known tube location the segmentation of the image can be initiated in the center of the tube. The dark area formed by red cells or visualization particles can be segmented by region growing methods or adaptive thresholding, generating a binary image containing a region corresponding to cell presence. The shape of the segmented area can be analyzed using the eigenvalues of the distribution, or alternatively by fitting a parametric shape such as an ellipse, or by calculating other shape parameters such as eccentricity or moments of inertia of the region. Also, the segmented region can be overlaid on the original image patch, and the intensity distribution and other intensity statistics of that region can be calculated.

Figure 11:
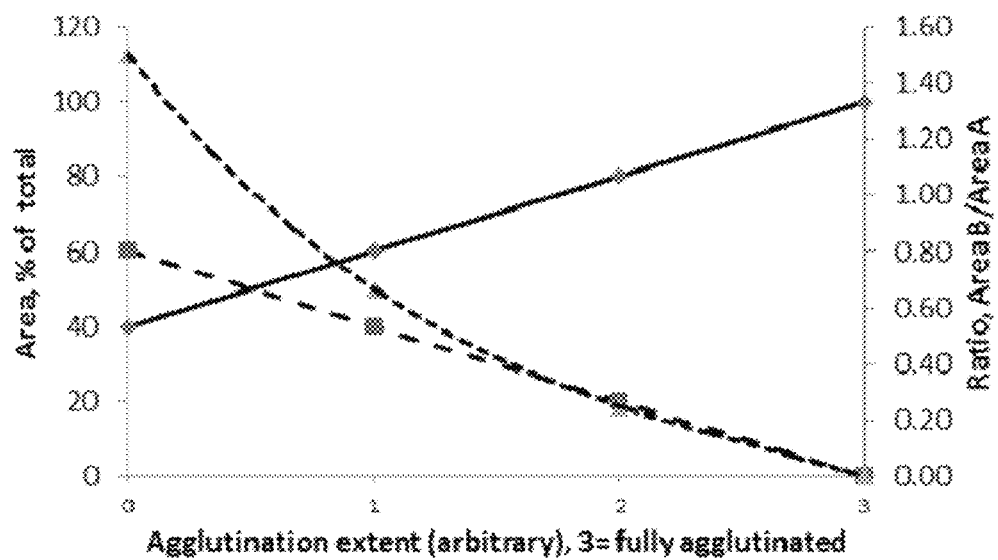
FIG. 11 shows a sample graph showing in an analysis as in FIG. 10, which depicts the relationship between % area of button or teardrop, agglutination extent, and the ratio of Area B to Area A. The line marked by diamonds is Area A, the line marked by squares is Area B, and the line marked by triangles is the ratio of Area B/Area A.

Sixth, when % of total area (A/(A+B) and B/(A+B); FIG. 11, line marked by diamonds and line marked by squares, respectively) is plotted against the extent of agglutination, a clear calibrate-able response is obtained. The ratio of areas (B/A) (FIG. 11, line marked by triangles) may give a more sensitive response to agglutination. Alternatively the total area over threshold may be used as a measure of agglutination. A measure of agglutination may also be obtained by combining shape and intensity information.

A4. General Considerations—Image Analysis of Bulk Movement of RBCs/Visualization Particles By using the methods provided herein for analyzing bulk movement of RBCs or visualization particles, an earlier and/or more accurate detection of agglutination and may be achieved compared to visual analysis of the same reactions by human observers.

In some embodiments, light sources may be used for gathering images of bulk movement for any of the methods provided herein. Front or back lighting may be used. Light sources may be white or LED (single color). Detectors can be of any imaging type, for example CCD or CMOS. Images may be taken at a single time or a video image series can be made with images taken at various intervals. In video, images may be taken at any interval, including 15/second, 10/second, 5/second, 1/second, 0.5/second, or 0.1/second. The methods of analysis described above are for the case where a single image is analyzed at a time. In some aspects, when video record is made of an agglutination assay the various signal parameters may be converted to rates of change over time (dS/dT).

In any of the methods provided herein, averaging across many pixels may be used to reduce random noise. Pixels may be averaged both in the x and y direction where x is the direction of the gravitational force. In some aspects, rows or columns of at least five adjacent pixels or square or rectangular zones with sides at least five pixels (25 pixels for a square zone) are averaged. In some example images provided herein, there are hundreds of pixels in each dimension, so averaging still provides data with good spatial resolution.

B. Image Analysis of Microscopic Images of RBCs/Visualization Particles

In one aspect, provided herein are image analysis methods for analyzing microscopic images of RBCs or visualization particles in suspension in an agglutination assay, in order to interrogate the fine structure of the cells or particles in suspension. Analysis of these images may provide information regarding agglutination of cells or particles in the suspension. In some aspects, these methods may permit detection of agglutination in a reaction sooner than may be detected by analysis of bulk movement of cells or particles. These methods may also be more reliable and adaptable to automation than the traditional methods that rely on visual interpretation.

In some embodiments, image analysis includes calculating the size of the erythrocyte-agglutinating particle clusters based on the center-to-center distance of individual erythrocytes captured in each of the images. The center-to-center distance of individual erythrocytes can be obtained based on, for example, internal calibration of the image with reference to the size of the red blood cells or visualization particle. In another example, it may be obtained based on absolute calibration of the optical system. Under microscopy, the erythrocytes may appear as bright solid circular spots or bright rings (depending on the illumination scheme). In either case, the center of each erythrocyte can be determined by calculating the centroid of the circle. Once the centroid of each circle is determined, the center-to-center distance may be calculated.

RBC center information can be used in conjunction with a "cut-off" distance to identify cells which are attracted to each other. A "cut-off distance" is typically a distance up to two times the cell diameter, although it may vary. In some embodiments, the "cut-off distance" is the distance of the cell diameter. In some embodiments, the "cut-off" distance is about 0.5, 1, 2, or 2.5 the diameter of an RBC. The cut-off distance can be determined from calibration or by an estimate of the distance over which RBCs experience attraction in an assay. Using the cut-off distance and information on cell locations, RBC clusters can be identified.

By "clusters" herein is meant a contiguous distribution of two or more cells, which are related to each other based on the determined cut-off distance. While the size of the cluster that may be detected using the assays disclosed herein will vary based on the components used in the assay, including the source of the erythrocytes, and the identity of the antisera and the virus, a cluster of as few as two erythrocytes may be detected using the assays. In particular aspects, clusters of less than about 3, 4, 5, 6, 7, 8, 9, 10, 20, 25, 30, 50, 75, or 100 erythrocytes may be detected using the assays provided herein.

In some embodiments, for every sample, the number of clusters of a certain size can be counted, and a histogram of cluster sizes calculated, generally as averaged over 10 images. This can be repeated for all samples. From the histogram of cluster sizes, a mean cluster size ($S_{mean}$) can be calculated using $$S_{mean} = \frac{\sum_i i^2 N_i}{\sum_i i N_i}$$

where $N_i$ is the number of clusters of size i where i is the number of RBCs in the cluster.

A more convenient way of representing the cluster sizes is by a so-called "Association Factor", defined as, $$AF = \frac{S_{mean}}{\min(S_{mean})}$$

where the normalization is done relative to the minimum value, which corresponds to the control sample. The mean cluster size can be plotted against the dilution factor for all samples to obtain a titer.

Figure 13:
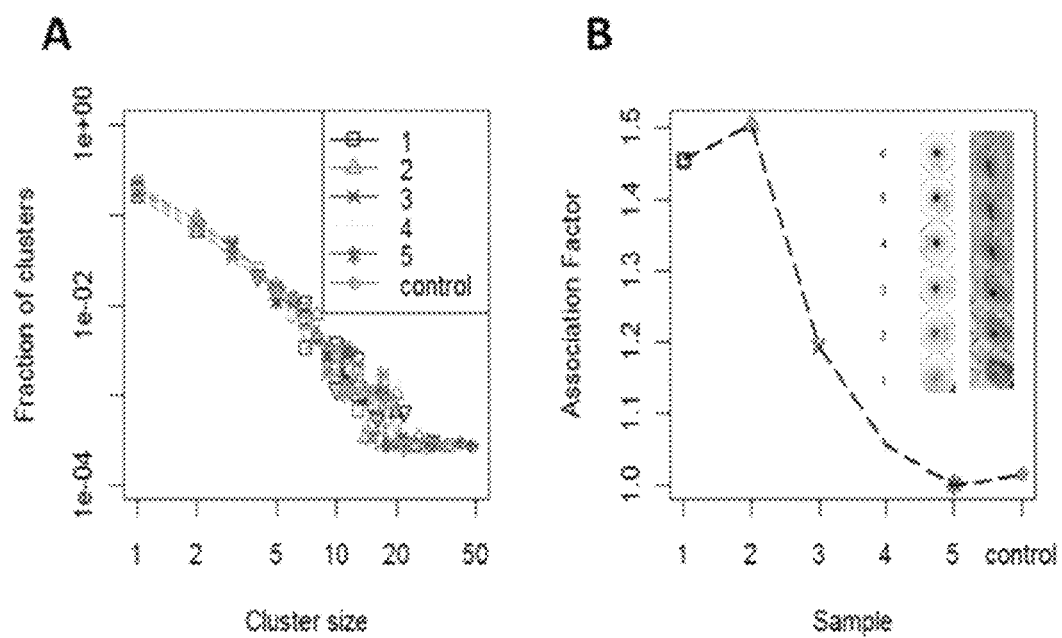
FIG. 13 shows distribution of cluster sizes for six samples, samples 1-5 and control (FIG. 13A) and the calculated association factor for each of the six samples (FIG. 13B). Inset in the right side graph is a macroscopic image of the same samples measured using the method of plate tilting and visual observation of the flow characteristics of packed red cells. The left column of the inset is an image of the wells before plate tilting, and the right column of the inset is an image of the wells after plate tilting.

Representative plots of cluster size histogram as well as the association factor are shown in FIG. 13. The plot in panel A shows the distribution of cluster sizes for six samples (samples 1 through 5 and a control). The association factor for all six samples is shown in FIG. 13 B. It is clearly seen that the samples with high virus concentrations (low dilutions, samples 1-2) show high values for the association factor, whereas samples 4, 5, and control show diminished values.

The transition between sample 2 and sample 4 is also quite evident. The inset in FIG. 13 B shows results from a typical HA assay, where the first column (left) shows images from an undisturbed titer plate, and the second column (right) shows images from a titer plate which has been tilted. It can be seen that samples 1-3 show some agglutination, while the other three samples display RBC flow, thereby suggesting non-agglutination. From these images, it would be concluded that the transition from agglutination to non-agglutination would be Sample #3, which is very close to the inflection point in the plot of the association factor. This demonstrates the agreement of results by methods provided herein with existing agglutination methods.

Thus, image analysis using methods of the disclosure can include calculating the size of the clusters based on the center-to-center distance of erythrocytes in the images, and the presence of a viral particle or an antibody in a sample can be determined based on the association factor derived from said cluster sizes.

The quantification of the viral particle or antibody concentration may be carried out by performing parallel assays using the biological sample to be tested and viral particle or antibody with known concentration or titer (calibration standards). The results can be plotted as the calibration standard may provide the calibration curve.

C. General Considerations—Image Capturing and Analysis

Methods of microscopy are well-known in the art, and described in U.S. Patent Publication Nos. 2009/0214114A1, 2011/0013821A1, 2008/0212865A1, and 2010/0183216A1, all incorporated herein by reference.

Methods of microscopy suitable for use with methods of the disclosure are also disclosed in U.S. Provisional Application No. 61/435,250, filed on Jan. 21, 2011, which is incorporated herein by reference.

One advantage of the method provided herein is to be able to use a small volume of samples. In some embodiments about 1-1.5 µL, of sample is used for analysis. In some embodiments, about or less than 1, 2, 3, 4, 5, 6, 7, 8, 9, 10, 15, 20, 25, 30, 35, 40, 45 or 50 µL of sample is used for analysis.

In some embodiments, the optical device comprises a camera, sensor, or detector. In some embodiments, the optical device is optically coupled to a microscope or the optical device comprises a sensor, detector, or camera optically coupled to a microscope.

In some embodiments, the image is captured using a CCD camera. The CCD camera may be a USB CCD camera. In some embodiments, the image is captured using a CMOS camera. The microscope stage can be moved to image a different field of view along the channel, and imaged.

In some embodiments, analysis of sample and the assay reaction products are performed using digital imaging. The assay reaction vessels may be aligned for measurement and scanned or imaged on a single operation. In some embodiments, this is achieved automatically by mechanical components. Assay reaction vessels may be located at defined locations in a cartridge, device, or system and moved to a scanner/camera for imagining and/or analysis. In some embodiments, the orientation of the reaction vessels is kept constant as the reaction vessels are moved to a scanner/camera. In some embodiments, a scanner/camera may be moved to a reaction vessel.

In some embodiments, the imaging region resides in a microfluidic channel. In some embodiments, the sample is taken and introduced into a microscopy cuvette containing a micro channel (also referred to herein as a microfluidic channel). In some embodiments, the micro channel can have a cross section of about 125 µm×1000 µm and be about 7 mm long. However, micro channel of other dimensions may also be used in the methods provided herein. The channel may be loaded onto a standard bright field microscope equipped with a broad-band light source and an objective (e.g., 10× objective). The microscope is adjusted such that the field of view is away from the side walls of the channel, and the image is in focus so as to clearly observe individual RBCs or visualization particles.

Following analysis of a sample, additional samples (e.g., with different virus/antibody concentrations) can be taken and loaded on to a new cuvette, and the image acquisition repeated. In some embodiments, about 10 images are collected for every titer. In some embodiments, less or more than 10 images are collected for every titer. The collected images are then processed precisely to locate RBC positions, with RBC centers detected from all images.

The images obtained by scanning or imaging can be a two-dimensional array of pixels, where each pixel comprises a plurality of intensity values corresponding to a distinct detection spectral region.

The illuminated background may emit white light of equal intensity over its entire surface. The light output may vary somewhat, producing a normal distribution of pixel intensities as detected by the imager/sensor. Exposure time may be the amount of time that the sensor pixels are permitted to collect photons before the value is read out. For a given amount of light, the readout value may be larger when the exposure time is made longer. This control may be the "coarse" control for the application. Gain may be the control adjusting the amount of amplification applied to the sensor signal. Increasing gain may increase the value of the signal from the sensor. Gain may be the "fine" control.

Analysis can be performed using an optical setup. The optical setup can include a light source, an aperture, and a sensor or a detector. In some embodiments the set up can include a camera, wherein the camera can be a web camera, the camera sensor can be CCD chip, the lens can be glass with a Lens-to-Object distance of anywhere from 5 to 100 mm, and the light source may be a white light source.

In an embodiment, disclosed herein is a reader assembly housing a detection assembly including a sensor or detector for detecting agglutination assays, and optionally, other assay types. The detection assembly may be above a reaction vessel or at a different orientation in relation to the reaction vessel based on, for example, the type of assay being performed and the detection mechanism being employed. The detection assembly can be moved into communication with the reaction vessel or the reaction vessel can be moved into communication with the detection assembly.

The optical detector/sensor can be any type of imaging sensor, such as CCDs. In some embodiments a detection assembly could include a plurality of fiber optic cables connected as a bundle to a CCD detector. The fiber optic bundle could be constructed of discrete fibers or of many small fibers fused together to form a solid bundle. Such solid bundles are commercially available and easily interfaced to CCD detectors.

A detector/sensor can also comprise a light source, such as a bulb or light emitting diode (LED). The light source can illuminate an assay in order to detect the results. The illumination sources can be lasers, single color LEDs, broad frequency light from fluorescent lamps or LEDs, LED arrays, mixtures of red, green, and blue light sources, phosphors activated by an LED, fluorescent tubes, incandescent lights, and arc sources, such as a flash tube. The detector can also comprise optics to deliver the light source to the assay, such as a lens or fiber optics.

The imaging area of a cuvette or reaction vessel may be designed so as to provide a sufficient number of cells for the application of interest. For example, counting the abundant RBCs may require counting of only 1000-2000 cells and hence a diluted sample and only a small imaging area in the cuvette.

A cuvette may be designed to be picked up by a standard pipetting mechanism in an automated fashion to allow the transfer of the cuvette to the imaging platform. The pipetting mechanism's tip ejector can eject the cuvette from the pipetting mechanism onto the imaging platform. Registration of cuvette to imaging platform may take place in two steps. Upon transfer of the cuvette to the imaging platform, static registration features on the cuvette may interface with mating features on the imaging platform to align the cuvette parallel to the imaging platform's optical axis (X,Y registration). Registration may then be completed by a mechanism located on the imaging platform. This mechanism may bias the cuvette against a planar surface perpendicular to the imaging platform's optical axis (Z registration), thereby constraining the sample within the imaging platform's focal range.

Methods of the disclosure provide for various illumination schemes: dark field and bright field. The modular nature of the setup also allows integration of phase-contrast and differential-interference contrast (DIC).

Bright field illumination may be achieved by the use of a white light source along with a stage-condenser to create Koehler illumination. A microscope stage may be connected to computer-controlled stepper motors to allow translation in the X and Y directions (e.g., horizontal directions). At every location, the desired number of images may be captured and the stage may be moved to the next XY position.

In some embodiments, provided herein are methods for determining the presence of an antibody, viral particle, or agglutinating particle, including capturing an image of agglutination.

In one embodiment, a method is provided for determining the presence of an antibody in a biological sample, wherein the antibody binds selectively to a viral particle, the method including: (a) incubating a mixture of erythrocytes, the viral particle, and the biological sample suspected of containing the antibody, under conditions permitting agglutination of the erythrocytes via interaction with the viral particle; and (b) detecting whether agglutination occurs in the mixture, wherein the absence of agglutination indicates the presence of said antibody, and wherein steps (a)-(b) take place in less than one hour. The presence of agglutination is evidenced by formation of erythrocyte-viral particle clusters, wherein the clusters exist in an imaging region (corresponding to a very small volume), and wherein the detecting step includes: (i) capturing a plurality of images of clusters at different locations of the imaging region with an optical device; and (ii) detecting the occurrence of agglutination based on analysis of the images. In some embodiments, step (a) includes incubating a mixture of the viral particle and the biological sample prior to adding the erythrocytes.

In another aspect, provided herein is a method for determining the presence of an antibody in a biological sample, wherein the antibody binds selectively to a viral particle, and the method includes: (a) incubating a mixture of erythrocytes, the viral particle, and the biological sample suspected of containing the antibody, under conditions permitting agglutination of the erythrocytes via interaction with the viral particle; and (b) capturing with the aid of an optical device an image (or a series of images taken over time) of the mixture, wherein the presence of an erythrocyte-viral particle cluster in the image indicates the occurrence of agglutination and lack of detectable amount of the antibody, and wherein the absence of the cluster indicates the lack of agglutination and the presence of detectable amount of the antibody. In some embodiments, step (a) includes incubating a mixture of the viral particle and the biological sample prior to adding the erythrocytes.

In another embodiment, provided herein is a method for determining the presence of a viral particle in a biological sample, including: (a) incubating a mixture of erythrocytes and a biological sample suspected of containing the viral particle, under conditions permitting agglutination of the erythrocytes via interaction with the viral particle; and (b) capturing with the aid of an optical device an image of the mixture, wherein the presence of an erythrocyte-viral particle cluster in the image indicates the occurrence of agglutination and the presence of detectable amount of the viral particle, and wherein the absence of clusters indicates the lack of agglutination and the lack of detectable amount of the viral particle.

In any of the methods provided above, the method may also be practiced where a visualization particle is used in place of erythrocytes, and/or where an agglutinating particle is used in place of a viral particle.

IV. Applications

In some embodiments, hemagglutination and hemagglutination inhibition assays provided herein may be used to measure viral antigens and anti-viral antibodies. The standard WHO hemagglutination inhibition method is excessively slow and has to be visually interpreted. In one aspect, provided herein are rapid, objectively read and well-standardized assays that may be used for obtaining rapid agglutination assay results so that immediate action can be taken to manage patient populations at risk and their therapy.

Identification of Individuals Suspected of Infection

In one aspect, a method is provided for identifying a subject infected with a pathogen and/or their contacts, so that the subject and/or their contacts can be isolated so the infection does not spread.

In some embodiments, a subject suspected of being in contact with a pathogen, such as a viral particle, is tested using the methods provided herein to determine the presence of the viral particle or if they contain an antibody that binds selectively to the viral particle. A biological sample, such as serum or plasma may be obtained from the subject and used for the testing.

Evaluation of Subjects and Immunization Programs

Detection and/or measurement of antibodies using methods of the disclosure are useful for determining effective immunization of a subject. The term "effective immunization" as used herein, means a state sufficient to induce a protective immune response in a subject. A subject may be deemed to be effectively immunized by the detection of antibodies against a given virus or viral antigen in a biological sample derived from the subject. Assessment of effective immunization may be made by measurement of a certain level of antibodies against a given virus or viral antigen in a biological sample derived from the subject.

Methods provided herein can also be used to evaluate immunization programs for effectiveness in immunizing a population or group of subjects. In some aspects, method provided herein may be used for evaluating immunization of a population or group of subject in a point of service test setting, such as schools, workplaces, or a subject's home.

In one aspect, provided herein is a method for determining the effective immunization of a subject, including: (a) obtaining a biological sample from a subject who has been immunized with a first dosage of a first vaccine against a viral particle; (b) incubating a mixture of erythrocytes, the viral particle, and the biological sample, under conditions permitting agglutination of the erythrocytes via interaction with the viral particle; and (c) determining the concentration of an antibody against the virus in the sample based on the clusters formed by the agglutination of the erythrocytes, and wherein steps (b)-(c) take place in less than about one hour.

In one aspect, provided herein is a method for determining the effective immunization of a subject, including: (a) obtaining a biological sample from a subject that has been immunized with a first dosage of a first vaccine against a viral particle; (b) incubating a mixture of erythrocytes, the viral particle, and the biological sample, under conditions permitting agglutination of the erythrocytes via interaction with the viral particle; (c) capturing with the aid of an optical device an image of the mixture; and (d) determining the concentration of an antibody against the viral particle in the biological sample based on the clusters formed by the agglutination of the erythrocytes, wherein the presence of an erythrocyte-viral particle cluster in the image indicates the occurrence of agglutination and lack of detectable amount of the antibody, and wherein the absence of the cluster indicates the lack of agglutination and the presence of a detectable amount of the antibody.

In any of the methods provided above, the method may also be practiced where a visualization particle is used in place of erythrocytes, and/or where an agglutinating particle is used in place of a viral particle.

Thus, methods provided herein can be used to measure the effectiveness of vaccination in real time and/or on-the-spot, and the vaccination dosage can be adjusted accordingly. Furthermore, alternate vaccines, if available can be used for subjects who are not responding to a vaccine under test. Therefore, vaccine providers can optimize the immunization schedule and dose.

Methods to Determine Blood Type

Methods of the disclosure may also be useful for determining blood type of a sample comprising erythrocytes. In some embodiments, antibodies against antigens of various blood types can be tested for their ability to induce hemagglutination in a sample comprising erythrocytes, thereby determining the blood type of the erythrocytes.

In some embodiments, methods are provided for determination of blood type of a sample comprising blood. Blood type can be determined using standard antibodies to A, B and Rh antigens and the addition of a whole blood sample. The antibodies specific to A, B and Rh antigens are well known, and are routinely used in blood testing. For example, if antibodies that bind the A blood group are added and agglutination occurs, the blood is either type A or type AB. To determine between type A or type AB, antibodies that bind the B group are added in a separate assay and if agglutination does not occur, the blood is type A. Methods of the disclosure can also be applied to cross-matching tests, to assess donor-recipient compatibility in blood transfusion. In cross-matching, agglutination occurring when donor red blood cells and recipient's serum or plasma are incubated together indicates that the donor blood is incompatible for that particular recipient.

Methods of the disclosure provide improvements for determination of blood type in a sample, and in some embodiments, the total amount time of carrying out the method is less than 500, 400, 300, 200, 180, 160, 140, 120, 100, 90, 75, 60, 45, 30, 15, 10, 5, 2, or 1 minute, or 30, 20, 10, 5, 3, or 1 second.

In some embodiments, the total amount time of carrying out the method is between 0.5 to 5 minutes.

V. Kits

In some embodiments, the disclosure also provides for a kit including: pre-fixed erythrocytes and a viral particle. Erythrocytes used for HA and HAI assays can be unstable, requiring time- and labor-intensive fresh preparation that also contributes to errors in assay reproducibility. In one embodiment, a kit of the disclosure provides pre-fixed erythrocytes and a viral particle, suitable for detecting or measuring antibodies to the virus without need for fresh preparation of erythrocytes. In another embodiment, a kit of the disclosure provides microspheres and a viral particle, suitable for detecting or measuring antibodies to the virus. In another embodiment, a kit of the disclosure provides visualization particles and agglutinating particles, suitable for detecting or measuring antibodies to the agglutinating particle. Kits disclosed herein may also provide assay reproducibility advantages by the use of standardized reagents.

Other reagents may also be provided with the kit, such as the various buffers and enzymes, BSA, and controls (negative and/or positive) which, for example, could be viral particles and/or antibody having known titer. Also, instructions for carrying out the assays may be provided with the kit.

EXAMPLES

Example 1

Pre-Treatment Method

Materials:

Neuraminidase 1 U (Sigma N7885-1UN, 3.78 U/mg protein); Buffer A: 100 mM Sodium Acetate pH 5.5, 0.15M NaCl, and 4 mM $CaCl_2$; Buffer B: 100 mM Sodium Phosphate pH 8.2, 1.5% Sodium Citrate; Neuraminidase Enzyme Solution [4 milliUnits (mU) Neuraminidase enzyme in 5 mL of Buffer A, for a final concentration of 0.8 mU/mL].

Method:

1. 4 volumes of Neuraminidase Enzyme Solution was added to 1 volume of serum (0.2 mL Neuraminidase+0.05 mL serum)

2. The mixture was incubated at 37±2° C. for 25 mins 3. 5 volumes of Buffer B was added to the mixture 4. The mixture was incubated at 56±2° C. for 5 mins to inactivate the Neuraminidase 5. The serum was allowed to cool to room temperature. The final dilution of the serum was 1:10 (start dilution in the serial dilution series for antibody titer determination).

Example 2

Hemagglutination Inhibition Assay—Comparison of Image Analysis Methods

Materials:

Influenza A H3N2/Brisbane/10/07 (4 HA U/50 µL) viral particles in diluent buffer; Diluent Buffer (Phosphate buffered saline pH 7.2, containing 0.05% sodium azide and 0.05% bovine serum albumin; PBS/A/BSA); human plasma containing antibody against Influenza B; and Glutaraldehyde-fixed Turkey-RBC (0.6% v/v) in diluent buffer.

Method:

1) To a microtiter plate 25 µL, of PBS/A/BSA was added to all wells, except for RBC control wells and the first well for the serial dilution of the treated sample containing antibody.

2) To the first well 50 µL, treated sample (serum or plasma) containing antibody (diluted 1/10 in treatment buffer) was added.

3) The sample was serially diluted by transferring 25 µL, of the sample from the first well to the adjacent well containing 25 µL, PBS/A/BSA. The steps were repeated until the last well in the series. This step is optional and may be advantageously replaced with by using a single dilution level.

4) To all wells containing the treated sample, 25 µL, Influenza B/Florida/04/06 virus diluted in PBS/A/BSA (4HA U/50 µL) was added.

5) 50 µL PBS/A/BSA was added to the control RBC wells.

6) The content of the wells were mixed by gently tapping the side walls of the microtiter plate.

7) 50 µL glutaraldehyde-fixed Turkey-RBC suspension (0.6%) prepared in PBS/A/BSA was added to all wells.

In the analysis of bulk movement of the reaction, the following steps (8-11) were also performed:

8) The content of the wells were mixed by gently tapping the side walls of the microtiter plate.

9) The plate was covered and incubated at room temperature for a total of about 15 minutes.

10) At 15 minutes the plate was read on the scanner and a final end-point image (FIG. 14B) was taken of the plate tilted at 45-60°.

11) The image was scanned (FIG. 14C), and the area and periphery of the dark regions corresponding to packed red cells are calculated In the image analysis of microscopic images, the following steps were performed after step 7):

12) A small sample (~1 or 2 µL) from the wells was pipetted directly into a cuvette, and imaged under the microscope.

13) Images were collected, and analyzed to calculate association factors of the RBCs.

Figure 14:
FIG. 14 shows comparison between (FIG. 14A) microscopic analysis of association factor, (FIG. 14B) macroscopic visual image of pelleting assay, (FIG. 14. C) macroscopic scanned image of pelleting assay subjected to threshold digitization, and (FIG. 14D) analysis of macroscopic scanned image of pelleting assay.
Figure 14D:
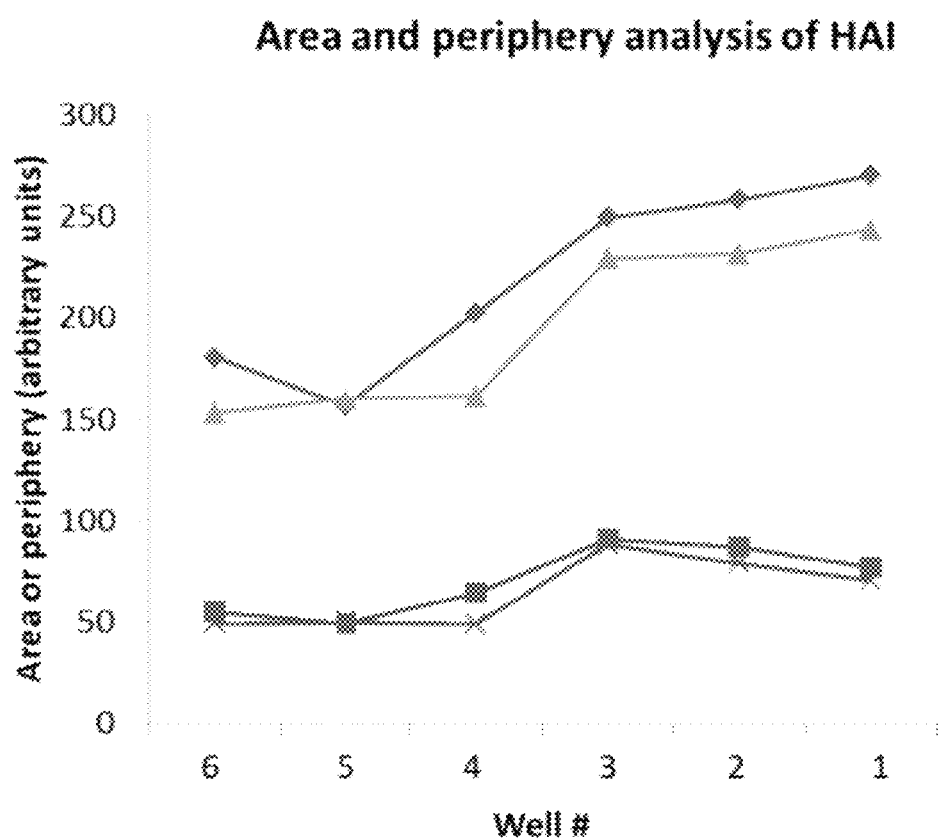
In FIG. 14D, the line marked by diamonds is area of cells in the right column of FIG. 14C, the line marked by triangles is the area of cells in the left column of FIG. 14C, the line marked by squares is the perimeter of cells in the right column of FIG. 14C, and the line marked by crosses is the perimeter of cells in the left column of FIG. 14C.

Using image analysis of microscopic images, the plot of association factor for different samples is shown in FIG. 14A. Using image analysis of bulk movement, the plot of area or periphery for the packed cells different samples is shown in FIG. 14D. Samples are numbered 1-6, and are in duplicate. FIG. 14B shows a macroscopic visual image of the wells of the pelleting assay after tilting. FIG. 14C shows a scanned image of FIG. 14B subjected to threshold digitization. The wells are numbered 1-6 starting from the bottom of the figure, and the right and left columns are duplicates of assays with the same level of dilution of sample. As shown in FIG. 14A, samples with high antibody concentrations (low dilutions, samples 1-3) show low values for the association factor, whereas samples 4, 5, and 6 (low antibody concentrations) show high values of the association factor. The transition between sample 3 and sample 4 is also quite evident. As shown in FIG. 14D, samples with high antibody concentrations (low dilutions, samples 1-3) show high values for perimeter and area of packed cells (i.e. many cells in the teardrop), whereas samples 4-6 (low antibody concentrations) show lower values for the perimeter and area of packed cells (i.e. fewer cells in the teardrop). The transition between sample 3 and sample 4 is also evident. In the macroscopic visual image of pelleting assay (FIG. 14B), it can be seen that samples 4-6 show agglutination, while samples 1-3 display RBC flow, thereby suggesting non-agglutination. From each of the above methods, it can be concluded that the transition from agglutination to non-agglutination is between Sample #3 and #4. Thus, this data demonstrates agreement between the methods for image analysis provided herein (both image analysis of microscopic images (FIG. 14A) and image analysis of bulk movement (FIG. 14D) with traditional analysis based on visual examination of agglutination assay wells (FIG. 14B).

Example 3

Microscopy-Based Method for RBC Agglutination Detection

A biological sample which may contain antibody was incubated with a virus for a specified period of time (≤5 minutes). After incubation, red blood cells were added to the sample and mixed. A portion (around 1-1.5 µL) of the sample was taken and introduced into a microscopy cuvette containing a microchannel. The microchannel had a cross section of 125 µm×1000 µm and is about 7 mm long. The channel was loaded onto a standard bright-field microscope equipped with a broad-band light source and a 10× objective. Each field of view corresponded to an area of ~700 µm×500 µm. The microscope was adjusted such that the field of view was away from the side-walls of the channel, and the image is in focus so as to clearly observe individual RBCs. The image was captured using a USB CCD camera. The microscope stage was moved along the axis of the channel to image a different field of view along the channel, and imaged. Around 10 fields of view were captured. Sample images are shown in FIG. 12.

Collected images were processed precisely to locate RBC positions. RBC centers were detected from all images. FIG. 12 shows representative images for two samples; Control sample (Left, panel A), which represents a non-agglutinated sample and an agglutinated sample (Right, panel B). While based on inspection of the images with the unaided eye it is difficult to differentiate the two samples, when RBC center information is used in conjunction with a "cut-off" distance, it is possible to identify cells which are bound to each other.

Example 4

Comparison of Traditional Pre-Treatment and a Pre-Treatment Method of the Disclosure A. Pre-treatment Traditional Method Receptor destroying enzyme (RDE) source was Sigma C8772 Cholera Filtrate crude extract from *Vibrio Cholerae*.

RDE was reconstituted with 5 mL sterile distilled water. 1 ml of the reconstituted RDE was diluted to 20 mL with calcium saline solution, pH 7.2. Four volumes of the diluted RDE were added to 1 volume of EDTA-anticoagulated human plasma (0.4 mL RDE+0.1 mL plasma). Samples were prepared in duplicate for four separate samples. For control (untreated) assays, 4 volumes calcium saline solution were added to 1 volume of plasma (0.4 mL calcium saline solution+0.1 mL plasma).

The mixtures were incubated for 30, 60, 360 minutes and overnight (>16 hours) at 37° C. The control was incubated overnight (>16 hours) at 37° C.

5 volumes of 1.5% sodium citrate (0.5 mL) were added to each sample. The samples were incubated at 56° C. for 30 minutes to inactivate the RDE. The serum was allowed to cool to room temperature. The final dilution of the treated serum was 1:10 (used as the starting dilution in the serial dilution series for antibody titer determination).

B. A Pre-treatment Method of the Disclosure

Neuraminidase source was 3.78 U/mg protein from Sigma. Neuraminidase Enzyme Solution was 4 mU Neuraminidase enzyme in 5 ml of Buffer A: 100 mM Sodium Acetate pH 5.5, 0.15M NaCl, and 4 mM $CaCl_2$ (0.8 mU/mL final concentration).

Four volumes of neuraminidase enzyme solution were added to 1 volume of plasma (0.2 mL Neuraminidase+0.05 mL plasma), and the mixture was incubated at 37° C. for 25 min. 5 volume of Buffer B (1.5% sodium citrate in Sodium phosphate pH8.2) (0.25 mL) were then added and the mixture was incubated at 56° C. for 5 min to inactivate the neuraminidase. The plasma was allowed to cool to room temperature. The final dilution of the plasma was 1:10 (start dilution in the serial dilution series for antibody titer determination)

C. Comparison

Figure 15:
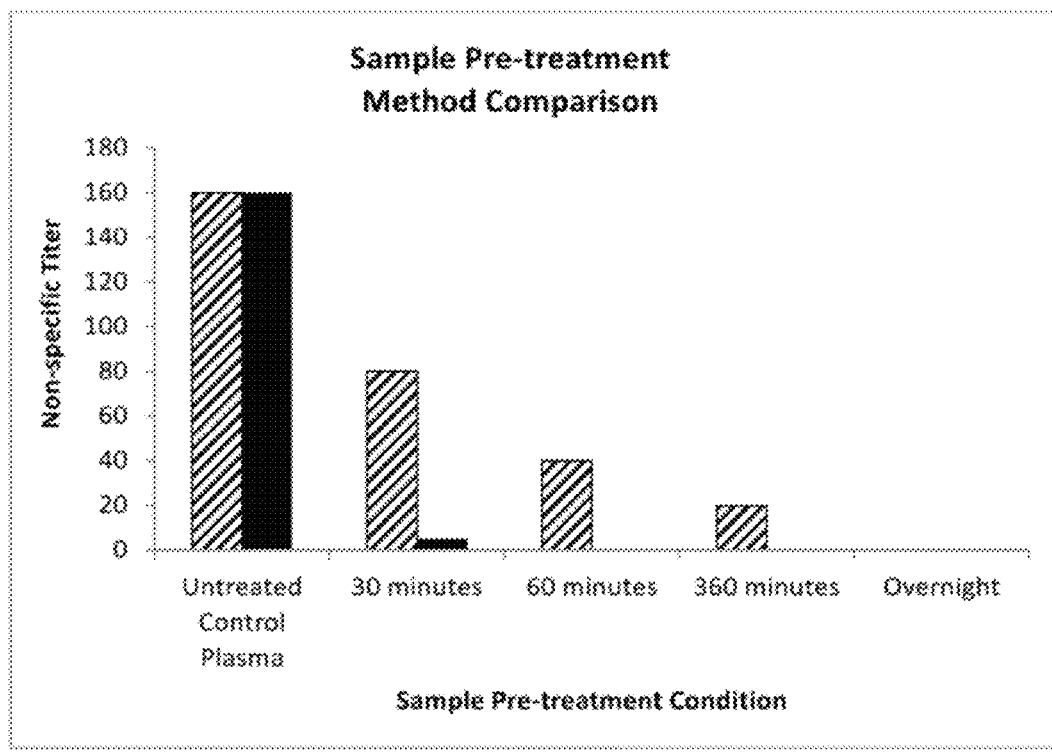
FIG. 15 shows comparison between pre-treatment with the traditional receptor-destroying enzyme (RDE) method (slashed fill) and a method using neuraminidase provided herein (solid fill).
Figure 16:
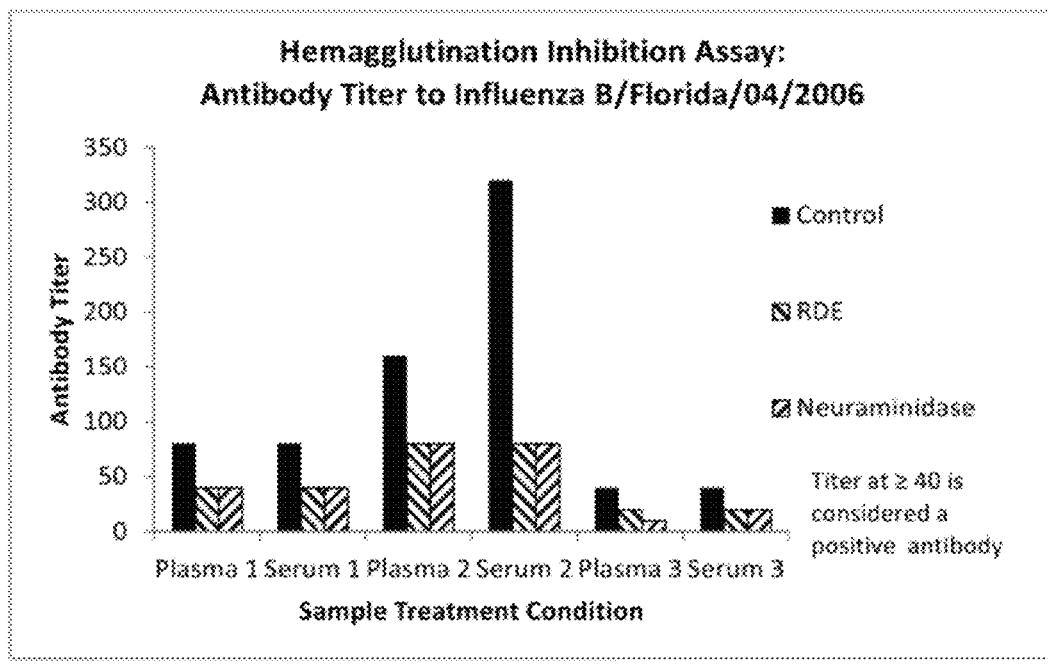
FIG. 16 shows comparison of pre-treatment of plasma samples, as labeled, with control, RDE method, and a neuraminidase method provided herein.

The results of comparative analysis are shown in FIG. 15. As seen, the non-specific reaction was eliminated with both methods, but the neuraminidase method of the disclosure (solid bars) was much faster than traditional method (slashed-fill bars). FIG. 16 shows the results of an HAI assay following various pre-treatment methods as described above and indicated. Samples were control (solid black bar), treated with RDE overnight (reversed-slash bar), or treated with neuraminidase for 25 minutes (forward-slash bar). Three paired plasma and serum samples (each from a single blood sample) were tested. Samples 1 and 3 were negative for viral antibody while sample 2 was positive. Both sample pre-treatment methods eliminated the false positive reactions while retaining the true positive reaction. As can be seen, the method of the disclosure is equally effective in both removal of false-positive reaction and retention of true positive reaction, and the disclosed method is much faster.

Example 5

Comparison of Methods of the Disclosure to Traditional HAI Method

In this experiment, certain methods of the disclosure for performing HAI assays were compared to traditional methods for performing HAI assays.

HAI Assays with a Single Viral Strain Antigen

In one experiment HAI assays were performed using Influenza A H1N1/California/04/2009 as the viral particle, and using biological sample from subjects that had been vaccinated against H1N1 virus.

The assays were performed as follows:

Pre-Treatment Step

For the traditional method samples, pretreatment of plasma samples from H1N1 vaccinated subjects was carried out as provided in Example 4, part A.

For the method of the disclosure samples, pretreatment of plasma samples from H1N1 vaccinated subjects was carried out as provided in Example 4, part B.

HAI Assay Step

For the traditional method samples, the HAI assay was carried out as provided in steps 1-10 of Example 2. The results of the assay were determined by unaided eye (visual) inspection of tilted wells.

For method of the disclosure samples, the HAI assay was carried out as provided in steps 1-7 plus 12-13 of Example 2. The results of the assay were determined by calculation of association factors of the samples based on image analysis of microscopic images of the agglutination reaction.

Analysis

Figure 17:
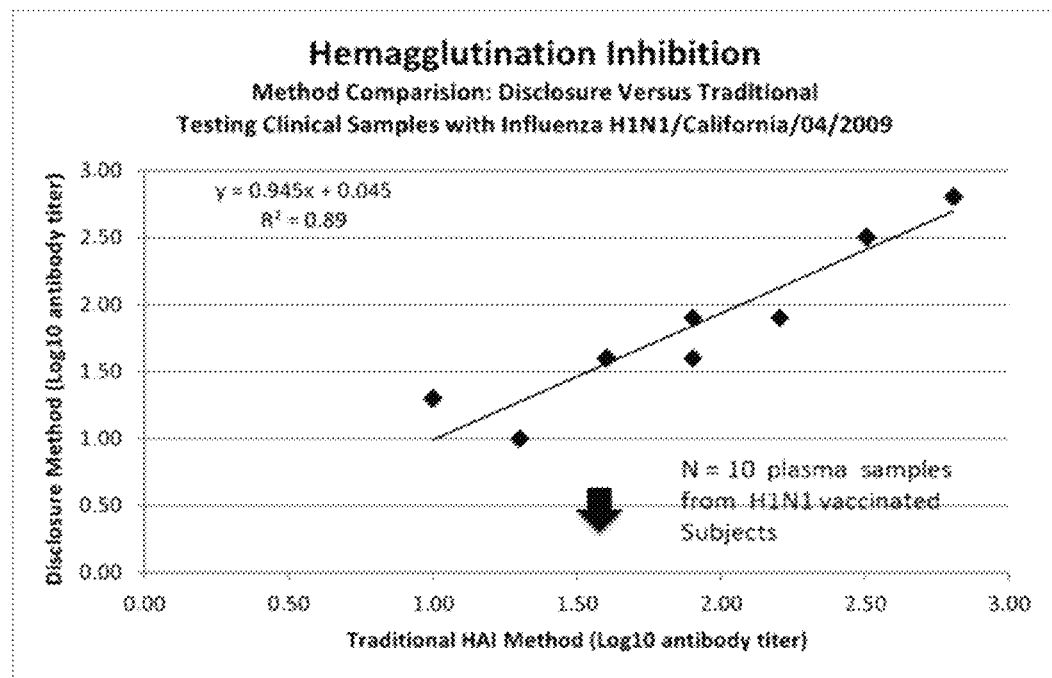
FIG. 17 shows antibody titer results from an HAI method of the disclosure plotted against results from the traditional HAI (hemagglutination assay inhibition) method.

The LOG of the antibody titer for the method of the disclosure samples was plotted against the LOG titer of the traditional method samples. As can be seen in FIG. 17, an excellent correlation was obtained and the slope and intercept value of the regression line indicates the congruence of the results of the two methods. $R^2$ value for the correlation line was 0.89, and N=10 plasma samples from H1N1 vaccinated subjects.

HAI Assay with a Multiple Viral Strain Antigens

In another experiment, assays were performed as above for the HAI Assay with a Single Viral Strain Antigen, except that assays were also performed with Influenza B (Influenza B/Florida/04/06) and Influenza A (Influenza A/H3N2/Brisbane/10/07), in addition to assays with Influenza A H1N1/California/04/2009 as the viral particles. The plasma samples were from individuals vaccinated with H1N1 (2009) pandemic virus, and who may have had previous exposure to the seasonal virus Influenza B and H3N2 viruses. As above, both traditional method and methods of the disclosure were used for both the pre-treatment and HAI assay steps.

Figure 18:
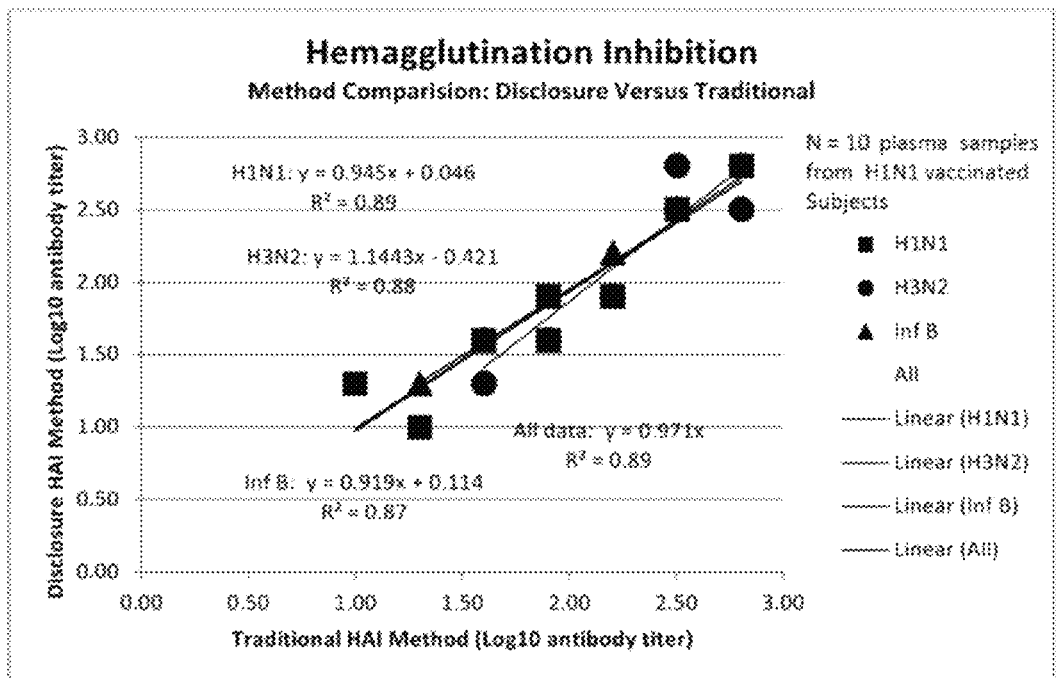
FIG. 18 shows antibody titer results from an HAI method of the disclosure plotted against results from the traditional HAI method, with three different viral antigens H1N1, H3N2, and Influenza B.

Referring to FIG. 18, assays for three viral strain antigens were used to assay for the corresponding antibodies. Results were plotted individually and then as an aggregated data set for all three strains. In all cases the regression statistics show equivalence of the two methods. No sample (out of 31) gave results more than one 2× dilution (the limit of resolution of the reference method) from the traditional method. This experiment also indicates that both methods are precise with an average imprecision of much less and one 2× dilution. Statistics of the comparison are given in Table 2 below.

TABLE 2

| | |
|---|---|
| Sample Count | 31 |
| LOG Max titer | 2.81 |
| LOG Min Titer | 1.00 |
| Mean LOG titer | 1.98 |
| Range, fold (Linear not LOG) | 65 |
| Average log difference | 0.16 |
| Standard error of the LOG estimate/LOG mean | 8.2% |
| (Equivalent to, fold) | 1.46 |

While the above is a complete description of the preferred embodiments of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Also, as used in the description herein and throughout the claims follow, terms of "include" and "contain" are open ended and do not exclude additional, unrecited elements or method steps. Finally, as used in the description herein and throughout the claims that follow, the meanings of "and" and "or" include both the conjunctive and disjunctive and may be used interchangeably unless the context expressly dictates otherwise. Thus, in contexts where the terms "and" or "or" are used, usage of such conjunctions do not exclude an "and/or" meaning unless the context expressly dictates otherwise.

What is claimed is:

1. A method for determining the presence of an antibody in a biological sample, wherein said antibody binds selectively to a viral particle, the method comprising:
    (a) incubating a mixture of erythrocytes, the viral particle, and the biological sample suspected of containing said antibody, under conditions permitting agglutination of the erythrocytes via interaction with said viral particle; and
    (b) detecting whether said agglutination occurs in said mixture, wherein the absence of said agglutination indicates the presence of said antibody, and
    wherein the presence of said agglutination is evidenced by formation of erythrocyte-viral particle clusters, wherein a cluster comprises a contiguous distribution of two or more erythrocytes having center-to-center distances between said erythrocytes of up to two times erythrocyte diameter, and wherein said clusters are captured in an imaging region of an optical device, and wherein said detecting step comprises:
    (i) capturing a plurality of images of said clusters at different locations of said imaging region with said optical device;
    (ii) calculating the size of said clusters based on the center-to-center distances between individual erythrocytes captured in each of said images; and
    (iii) detecting the occurrence of said agglutination based on analysis of said cluster sizes calculated from the plurality of images obtained using the optical device.

2. The method of claim 1, wherein said erythrocytes are pre-fixed.

3. The method of claim 1, wherein said biological sample comprises plasma or serum.

4. The method of claim 1, wherein said biological sample is pre-treated with neuraminidase.

5. The method of claim 4, wherein said pre-treatment is carried out by incubating said biological sample with neuraminidase, and wherein the final concentration of the neuraminidase in the mixture is between 0.1 and 1.5 U/L.

6. The method of claim 4, wherein said pre-treatment is carried out by incubating said sample with active neuraminidase for less than 30 minutes.

7. The method of claim 1, wherein said biological sample is serially diluted prior to step (a).

8. The method of claim 1, wherein said optical device comprises a camera.

9. The method of claim 1, wherein said optical device comprises a microscope.

10. The method of claim 1, wherein calculating the size of said clusters based on the center-to-center distance of individual erythrocytes captured in each of said images comprises calculating normalized cluster size values.

11. The method of claim 1, wherein said step (a) comprises incubating a mixture of said viral particle and said biological sample before adding said erythrocytes.

12. A method for determining the presence of a viral particle in a biological sample, comprising:
    (a) incubating a mixture of erythrocytes and a biological sample suspected of containing said viral particle, under conditions permitting agglutination of the erythrocytes via interaction with said viral particle; and
    (b) detecting whether said agglutination occurs in said mixture, wherein the presence of said agglutination indicates the presence of said viral particle,
    and wherein the presence of said agglutination is evidenced by formation of erythrocyte-viral particle clusters, wherein a cluster comprises a contiguous distribution of two or more erythrocytes having center-to-center distances between said erythrocytes of up to two times erythrocyte diameter, and wherein said clusters are captured in an imaging region of an optical device, and wherein said detecting step comprises:
(i) capturing a plurality of images of said clusters at different locations of said imaging region with said optical device;
(ii) calculating the size of said clusters based on the center-to-center distances between individual erythrocytes captured in each of said images; and
(iii) detecting the occurrence of said agglutination based on analysis of said cluster sizes calculated from the plurality of images obtained using the optical device.

13. The method of claim 12, wherein said erythrocytes are pre-fixed.

14. The method of claim 12, wherein said optical device comprises a camera.

15. The method of claim 12, wherein said optical device comprises a microscope.

16. The method of claim 12, wherein calculating the size of said clusters based on the center-to-center distance of individual erythrocytes captured in each of said images comprises calculating normalized cluster size values.

17. A method for determining the presence of an antibody in a biological sample, wherein said antibody binds selectively to a viral particle, the method comprising:
(a) incubating a mixture of visualization particles, the viral particle, and the biological sample suspected of containing said antibody, under conditions permitting agglutination of the visualization particles via interaction with said viral particle; and
(b) detecting whether said agglutination occurs in said mixture, wherein the absence of said agglutination indicates the presence of said antibody, and
wherein the presence of said agglutination is evidenced by formation of visualization particle-viral particle clusters, wherein a cluster comprises a contiguous distribution of two or more visualization particles having center-to-center distances between said visualization particles of up to two times visualization particle diameter, and wherein said clusters are captured in an imaging region of an optical device, and wherein said detecting step comprises:
(i) capturing a plurality of images of said clusters at different locations of said imaging region with said optical device;
(ii) calculating the size of said clusters based on the center-to-center distances between individual visualization particles captured in each of said images; and
(iii) detecting the occurrence of said agglutination based on analysis of said cluster sizes calculated from the plurality of images obtained using the optical device.

18. The method of claim 17, wherein the visualization particle is a microsphere.

19. The method of claim 18, wherein the microsphere is a bead.

20. The method of claim 18, wherein the microsphere is coated with a receptor that binds to a viral particle.

* * * * *